US007659366B2

(12) United States Patent
Ellen et al.

(10) Patent No.: US 7,659,366 B2
(45) Date of Patent: Feb. 9, 2010

(54) PEPTIDE WITH PUTATIVE ROLE IN CYTOSKELETAL PROTECTION

(76) Inventors: Richard P. Ellen, 99 Cranbrooke Avenue, Toronto, Ontario (CA) M5M 1M6; Mohsen Amin, 1017-15 Northtown Way, Toronto, Ontario (CA) M2N 7A2

(*) Notice: Subject to any disclaimer, the term of this patent is extended or adjusted under 35 U.S.C. 154(b) by 0 days.

(21) Appl. No.: 11/609,896

(22) Filed: Dec. 12, 2006

(65) Prior Publication Data

US 2007/0167366 A1 Jul. 19, 2007

Related U.S. Application Data

(60) Provisional application No. 60/789,158, filed on Apr. 5, 2006, provisional application No. 60/749,377, filed on Dec. 12, 2005.

(51) Int. Cl.
C07K 7/00 (2006.01)
(52) U.S. Cl. .................... 530/328; 530/324; 514/2
(58) Field of Classification Search ................ 514/2; 530/324, 328
See application file for complete search history.

(56) References Cited

OTHER PUBLICATIONS

Aktories, K. and Barbieri, J.T. (2005) Bacterial cytotoxins: targeting eukaryotic switches. *Nat Rev Microbiol.* 3: 397-410.
Allport, J.R., Lim, Y.C., Shipley, J.M., Senior, R.M., Shapiro, S.D., Matsuyoshi, N., et al (2002) Neutrophils from MMP-9- or neutrophil elastase-deficient mice show no defect in transendothelial migration under flow in vitro. *J Leukoc Biol.* 71: 821-828.
Amin M, Ho AC, Lin JY, Batista da silva AP, Glogauer M, Ellen RP (2004). Induction of de novo subcortical actin filament assembly by *Treponema denticola* major outer sheath protein. *Infect Immun* 72:3650-4.
Batista da Silva AP, Lee W, Bajenova E, McCulloch CA, Ellen RP (2004). The major outer sheath protein of *Treponema denticola* inhibits the binding step of collagen phagocytosis in fibroblasts. *Cell Microbiol* 6:485-98.
Bubb MR, Senderowicz AM, Sausville EA, Duncan KL, Korn ED (1994). Jasplakinolide, a cytotoxic natural product, induces actin polymerization and competitively inhibits the binding of phalloidin to F-actin. *J Biol Chem* 269:14869-71.
Bubb MR, Spector I, Beyer BB, Fosen KM (2000). Effects of Jasplakinolide on the Kinetics of Actin Polymerization. *J Biol Chem* 275:5163-70.

Caron, E., Crepin, V.F., Simpson, N., Knutton, S., Garmendia, J. and Frankel, G. (2006) Subversion of actin dynamics by EPEC and EHEC. *Curr Opin Microbiol.* 9: 40-45.
Chrzanowska-Wodnicka, M. and Burridge, K. (1996) Rho-stimulated contractility drives the formation of stress fibers and focal adhesions. *J Cell Biol.* 133: 1403-1415.
Cossart, P. (1997) Host/pathogen interactions. Subversion of the mammalian cell cytoskeleton by invasive bacteria. *J Clin Invest.* 99: 2307-2311.
Cossart, P. and Lecuit, M. (1998) Interactions of *Listeria monocytogenes* with mammalian cells during entry and actin-based movement: bacterial factors, cellular ligands and signaling. *Embo J.* 17: 3797-3806.
Cox DL, Akins DR, Porcella SF, Norgard MV, Radolf JD (1995). Treponema pallidum in gel microdroplets: a novel strategy for investigation of treponemal molecular architecture. *Mol Microbiol* 15:1151-64.
Cox, E.A., Sastry, S.K. and Huttenlocher, A. (2001) Integrin-mediated adhesion regulates cell polarity and membrane protrusion through the Rho family of GTPases. *Mol Biol Cell.* 12: 265-277.
Di Ciano-Oliveira C, Sirokmany G, Szaszi K, Arthur WT, Masszi A, Peterson M, Rotstein OD, Kapus A (2003). Hyperosmotic stress activates Rho: differential involvement in Rho kinasedependent MLC phosphorylation and NKCC activation. *Am J Physiol Cell Physiol* 285:C555-66.
Ellen RP, Galimanas VB (2005). Spirochetes at the forefront of periodontal infections. *Periodontology* 2000 38:12-32.
Fabian I, Shur I, Bleiberg I, Rudi A, Kashman Y, Lishner M (1995). Growth modulation and differentiation of acute myeloid leukemia cells by Jasplakinolide. *Exp. Hematol* 23:583-7.
Fenno JC, Muller KH, McBride BC (1996). Sequence analysis, expression, and binding activity of recombinant major outer sheath protein (Msp) of *Treponema denticola*. *J Bacteriol* 178:2489-97.
Finlay, B.B. and Cossart, P. (1997) Exploitation of mammalian host cell functions by bacterial pathogens. *Science.* 276: 718-725.
Finlay, B.B. and Hancock, R.E. (2004) Can innate immunity be enhanced to treat microbial infections? *Nat Rev Microbiol.* 2: 497-504.
Freshney, R.I. (2005) *Culture of animal cells: a manual of basic technique.* Hoboken, N.J.: WileyLiss: 177-193.
Gouin, E., Welch, M.D. and Cossart, P. (2005) Actin-based motility of intracellular pathogens. *Curr Opin Microbiol.* 8: 35-45.

(Continued)

*Primary Examiner*—David Lukton
(74) *Attorney, Agent, or Firm*—Woodcock Washburn LLP

(57) ABSTRACT

The invention relates to a novel peptide conjugate useful for stabilizing the actin cytoskeleton of mammalian cells. More particularly, the invention relates to a conjugate of a peptide found within the sequence of a bacterium's major outer sheath protein and bovine serum albumin (BSA), and the use of this conjugate for stabilizing the actin cytoskeleton of mammalian cells, and for preventing or controlling the migration of mammalian cells.

9 Claims, 27 Drawing Sheets

OTHER PUBLICATIONS

Haapasalo M, Muller K-, Uitto B-J, leung WK, and McBride (1992). Characterization, cloning, and binding properties of the major 53-kilodalton *Treponema denticola* surface antigen. *Infect Immun* 60:2058-65.

Hayward, R.D., Leong, J.M., Koronakis, V. and Campellone, K.G. (2006) Exploiting pathogenic *Escherichia coli* to model transmembrane receptor signalling. *Nat Rev Microbiol.* 4: 358-370.

Holzinger A, Meindl U (1997). Jasplakinolide, a novel actin targeting peptide, inhibits cell growth and induces actin filament polymerization in the green alga *Micrasterias*. *Cell Motil Cytoskel* 38: 365-372.

Lee E, Shelden EA, Knecht DA (1998). Formation of F-actin aggregates in cells treated with actin 34 stabilizing drugs. *Cell Motil Cytoskel* 39:122-33.

Mathur J, Spielhofer P, Kost B, Chua N (1999). The actin cytoskeleton is required to elaborate and maintain spatial patterning during trichome cell morphogenesis in *Arabidopsis thaliana*. Development 126:5559-5568.

Maul, R.S., Song, Y., Amann, K.J., Gerbin, S.C., Pollard, T.D. and Chang, D.D. (2003) EPLIN regulates actin dynamics by cross-linking and stabilizing filaments. *J Cell Biol.* 160: 399-407.

Patel, J.C. and Galan, J.E. (2005) Manipulation of the host actin cytoskeleton by *Salmonella*—all in the name of entry. *Curr Opin Microbiol.* 8: 10-15.

Pender, N. and McCulloch, C.A. (1991) Quantitation of actin polymerization in two human fibroblast sub-types responding to mechanical stretching. *J Cell Sci.* 100 (Pt 1): 187-193.

Potocky, T.B., Menon, A.K. and Gellman, S.H. (2003) Cytoplasmic and nuclear delivery of a TAT derived peptide and a beta-peptide after endocytic uptake into HeLa cells. *J Biol Chem.* 278: 5018850194.

Puthengady Thomas, B., Sun, C.X., Bajenova, E., Ellen, R.P. and Glogauer, M. (2006) Modulation of human neutrophil functions in vitro by *Treponerna denticola* major outer sheath protein. *Infect Immun.* 74: 1954-1957.

Qian, Z.M., Li, H., Sun, H. and Ho, K. (2002) Targeted drug delivery via the transferrin receptormediated endocytosis pathway. *Pharmacol Rev.* 54: 561-587.

Ridley, A.J. (2001) Rho GTPases and cell migration. *J Cell Sci.* 114: 2713-2722.

Rosado JA, Sage SO (2000). A role for the actin cytoskeleton in the initiation and maintenance of store-mediated calcium entry in human platelets. *Trends Cardiovasc Med* Nov; 10(8):327-32.

Rottner, K., Stradal, T.E. and Wehland, J. (2005) Bacteria-host-cell interactions at the plasma membrane: stories on actin cytoskeleton subversion. *Dev Cell.* 9: 3-17.

Saito, S.Y., Feng, J., Kira, A., Kobayashi, J. and Ohizumi, Y. (2004) Amphidinolide H, a novel type of actin-stabilizing agent isolated from dinoflagel late. *Biochem Biophys Res Commun*. 320: 961-965.

Senderowicz AM, Kaur G, Sainz E, Laing C, Inman WD, Rodriguez J, Crews P, Malspeis L, Grever MR and Sausville EA .Jasplakinolide's inhibition of the growth of prostate carcinoma cells in vitro with disruption of the actin cytoskeleton (1995). JNCI 87:46-51.

Seshadri R, et al., (2004). Comparison of the genome of the oral pathogen *Treponema denticola* with other spirochete genomes. Proc Natl Acad Sci USA 101:5646-51.

Thomas BP, Sun CX, Bajenova E, Ellen RP, Glogauer M. (2006). Modulation of human neutrophil functions in vitro by *Treponema denticola* major outer sheath protein (Msp). *Infect Immun.* 74(3): 1954-1957.

Tjabringa, G.S., Aarbiou, J., Ninaber, D.K., Drijthout, J.W., Sorensen, O.E., Borregaard, N., et al (2003) The antimicrobial peptide LL-37 activates innate immunity at the airway epithelial surface by transactivation of the epidermal growth factor receptor. *J lmmunol.* 171: 6690-6696.

Usui, T., Kazami, S., Dohmae, N., Mashimo, Y., Kondo, H., Tsuda, M., et al (2004) Amphidinolide h, a potent cytotoxic macrolide, covalently binds on actin subdomain 4 and stabilizes actin filament. *Chem Biol.* 11: 1269-1277.

Wang Q, Ko KS, Kapus A, McCulloch C, Ellen RP (2001). A spirochete surface protein uncouples store-operated calcium channels in fibroblasts. J Biol Chem 276:23056-64.

Weiner, D.J., Bucki, R. and Janmey, P.A. (2003) The antimicrobial activity of the cathelicidin LL37 is inhibited by F-actin bundles and restored by gelsolin. *Am J Respir Cell Mol Biol.* 28: 738-745.

Work, T.S. and Burdon, R.H. (1980) *Laboratory techniques in biochemistry and molecular biology*. Amsterdam: Elsevier / North-Holland Biomedical Press. pp. 79-82.

Zigmond, S.H. (1988) Orientation chamber in chemotaxis. *Methods Enzymol.* 162:65-7.

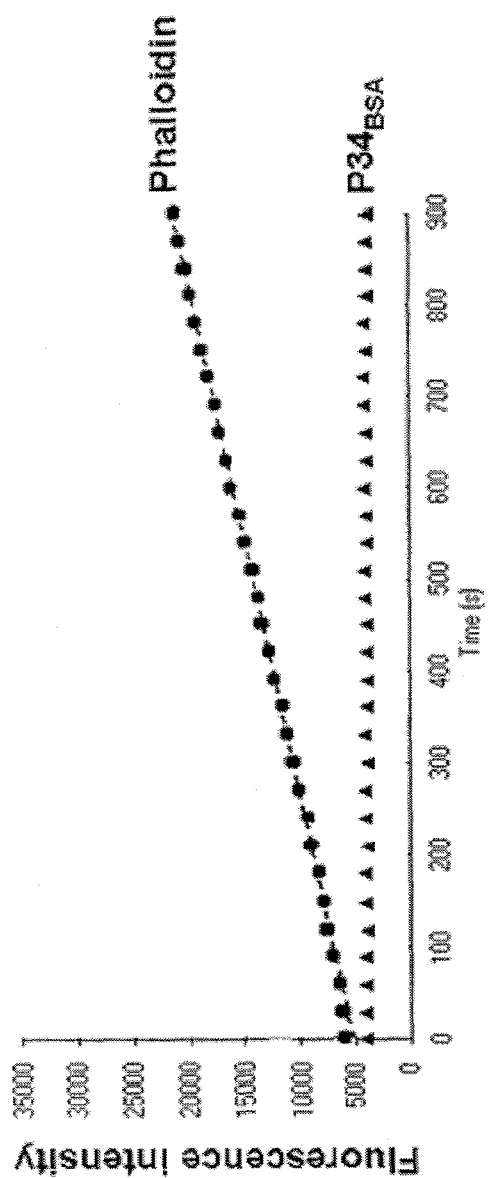
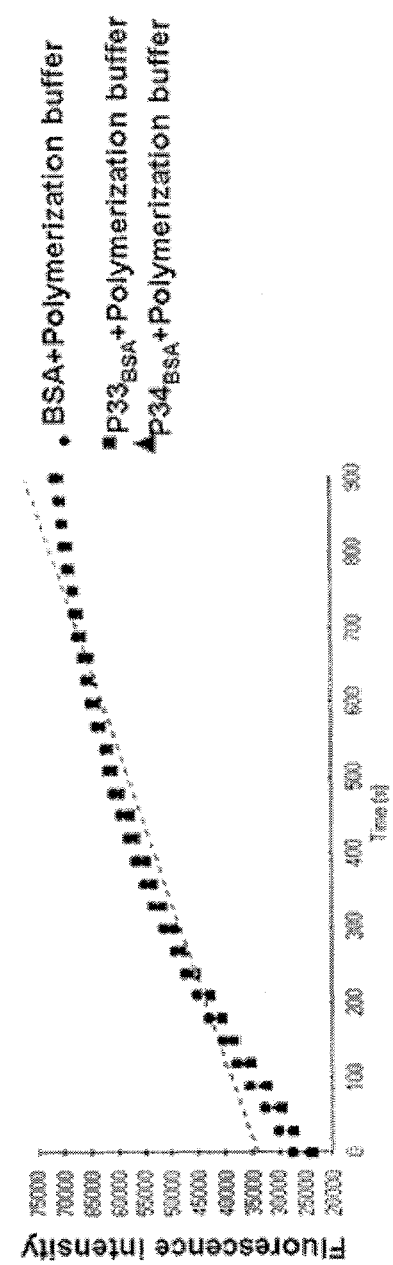
Figure 18A
Figure 18B

SEQUENCE LISTING

```
<160> NUMBER OF SEQ ID NOS: 5

<210> SEQ ID NO 1
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 1

Tyr Ala Gly Xaa Asp Xaa Asn Asn Xaa Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Tyr Ala Gly Lys Asp Lys Asn Asn Lys Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Leu Gly Val Asn Leu Ala Tyr Arg Phe Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic construct

<400> SEQUENCE: 4

Gly Ala Thr Tyr Tyr Lys Gln Asn Gly Ile
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Gly Ser Asn Pro Asp Lys Pro Tyr Leu Gly
1               5                   10
```

US 7,659,366 B2

PEPTIDE WITH PUTATIVE ROLE IN CYTOSKELETAL PROTECTION

CROSS-REFERENCE TO RELATED APPLICATIONS

The present application claims priority to U.S. Provisional Application No. 60/749,377 (Filing Date: Dec. 12, 2005) and U.S. Provisional Application No. 60/789,158 (Filing Date: Apr. 5, 2006), the contents of which are incorporated herein by reference in their entirety.

FIELD OF THE INVENTION

The invention relates to a novel peptide conjugate useful for stabilizing the actin cytoskeleton of mammalian cells. More particularly, the invention relates to a conjugate of a peptide found within the sequence of a bacterium's major outer sheath protein and bovine serum albumin (BSA), and the use of this conjugate for stabilizing the actin cytoskeleton of mammalian cells, and for preventing or controlling the migration of mammalian cells.

BACKGROUND OF THE INVENTION

The cellular cytoskeleton functions to maintain the spatial shape and volume of mammalian cells; it is crucial for functions such as locomotion (migration), endocytosis, phagocytosis, and mechanoprotection. Actin is one of the key proteins of the cytoskeleton, and the physiologic assembly and disassembly of actin filaments in response to regulatory signals maintains homeostasis of cellular functions and responds to external stresses to protect the cell. Actin filaments are often found in bundles called stress fibers that terminate in focal complexes at the plasma membrane, where they communicate with the extracellular matrix through focal adhesions and associated membrane proteins called integrins. Cells move by remodeling actin filaments at their leading edge. Inflammatory cells like neutrophils and macrophages require actin filament assembly to migrate to sites of infection or injury and to engulf microorganisms or other foreign objects. Cells like fibroblasts that maintain the integrity of connective tissue extracellular matrix (ECM; collagen, for example) require actin filament assembly to migrate to heal wounds and to phagocytose collagen to maintain homeostasis of the ECM. Epithelial cells require actin filament assembly to migrate over wounds and to maintain cell-cell junctions in a protective barrier that protects the underlying connective tissue from microbes and their products. So, the cytoskeleton is a central part of the cellular machinery in virtually all cells and all tissues of the body.

Phalloidin, jasplakinolide and amphidinolide H are three actin-stabilizing agents that bind to actin filaments and aggregate them in vitro (Holzinger and Meindl, 1997; Lee et al., 1998; Saito et al., 2004). Besides their application in investigating actin dynamics and actin dependant events in mammalian cells, phalloidin has become a very valuable reagent in cytoskeletal imaging techniques when conjugated to fluorescent dyes. Similar to phalloidin, Jasplakinolide induces actin polymerization and stabilizes pre-existing actin filaments in vitro (Bubb et al., 1994, Holzinger, 1997; Mathur et al., 1999; Rosado and Sage, 2000, Bubb et al., 2000). Jasplakinolide differs from phalloidin, in that it is cell permeant. It gets into the cell and can therefore be more easily used for in vitro experiments using cells in culture. Jasplakinolide is a naturally occurring cell permeable cyclic peptide, produced by a sponge, *Jaspis johnstoni*. It is known to inhibit the growth of prostate carcinoma cell lines in vitro (Senderowicz et al., 1995), and to prevent the self-renewal of acute myeloid leukemia cells (Fabian et al., 1995). In each of these reports, the effects of Jasplakinolide were attributed to its ability to bind and stabilize actin filaments.

There are a number of laboratory reagents, like Cytochalasin, that are highly useful in research because they are cytoskeletal inhibitors, but there are fewer laboratory reagents with cytoskeletal stabilizing effects. The above-noted actin-stabilizing reagents come from living organisms: mushrooms, sponges, and algae. Obtaining such agents from biological sources involves labour-intensive procedures. Thus, the development of new synthetically accessible laboratory reagents with cytoskeletal stabilizing effects is highly desirable.

Over the past 15 years, there has been a great expansion of knowledge about how bacteria exploit or perturb the host cell cytoskeleton. Numerous bacterial proteins that act on cytoskeleton-regulating signal transduction pathways have been identified and characterized (Finlay and Cossart, 1997; Cossart, 1997; Cossart and Lecuit, 1998; Aktories and Barbieri, 2005; Patel and Galan, 2005; Rottner et al., 2005; Caron et al., 2006). Notably, bacterial agonists of cytoskeletal remodeling are now being considered for their potential applications in modulating membrane receptor activity and innate immunity, concentrating mostly on bacteria that are exogenous pathogens (Finlay and Hancock, 2004; Hayward et al., 2006). The same strategies applied to indigenous bacteria, which have evolved in concert with the host, would theoretically expand the probability of identifying potential target molecules.

Cellular turnover among gingival epithelial cells and ECM turnover in the periodontal connective tissues are among the most rapid in the body due to these tissues being in constant proximity to a large mass of bacteria that colonize on the teeth as a subgingival biofilm. *Treponema denticola* is one of the most prominent bacteria that colonize at the interface of the bacterial biofilm and the gingival tissues, and it is a key organism associated with progressive chronic periodontitis (Ellen and Galimanas, 2005).

The major surface antigen of *T. denticola* is known as the major outer sheath protein (Msp). This protein was first characterized in McBride's laboratory at the University of British Columbia (Haapasalo et al, 1992). The full gene was cloned, sequenced, and investigated in detail, as reported in subsequent publications (Fenno et al., 1996, 1997). For over a decade, Applicants have investigated the effects of *T. denticola* and more recently Msp on oral host cells, mostly gingival fibroblasts and epithelial cells, and recently neutrophils. Applicants' laboratory is the only laboratory that has reported on the cytoskeletal effects of Msp and of this bacterium.

Current literature (Amin et al., 2004; Batista da Silva et al, 2004, Wang et al., 2001) suggests that the major outer sheath protein (Msp) of the indigenous oral spirochete *Treponema denticola* induces significant cytoskeletal reorganization through disassembly of actin filaments and stress fibers ventrally near the middle of the cell, accompanied by the assembly of a mesh of subcortical actin filaments that disrupt some cellular functions. A few recent papers that are highly novel show that cell exposure to Msp uncouples store operated calcium channels (SOCs) and prevents the normal affinity modulation (cellular adhesion, spreading, and migration) when fibroblasts contact extracellular collagen (see FIG. 1). Both effects appear to involve Msp-induced reorganization of the actin cytoskeleton, including assembly of a subcortical mesh of actin filaments. These novel discoveries are published in Wang et al. 2001, Paes da Silva et al. 2004, and Amin et al. 2004 and references therein. Msp also inhibits chemotaxis in neutrophils and suppresses their calcium and actin responses to chemoattractants (Puthengady Thomas et al., 2006). Since these publications, Applicants have been trying to seek ways to determine the active peptide domains of Msp that determine its cytoskeletal effects.

During the course of these studies, Applicants have surprisingly and unexpectedly produced a novel peptide conjugate with cytoskeletal stabilizing effects.

SUMMARY OF THE INVENTION

In one aspect, the invention provides a peptide conjugate comprising a carrier and at least one peptide, wherein said at least one peptide has the peptide sequence YAGXDXNNXA (SEQ ID NO:1), and X is a positively charged amino acid residue. In another aspect, X is a lysine residue.

In another aspect, the invention provides a peptide conjugate comprising a carrier, such as bovine serum albumin, and at least one peptide, wherein said at least one peptide has the peptide sequence YAGKDKNNKA (SEQ ID NO:2). The average ratio of the conjugation is 6:1.

In another aspect, the invention provides the use of the novel peptide conjugates for stabilizing the actin cytoskeleton of mammalian cells, such as fibroblasts.

In yet another aspect, the invention provides a method for preventing or controlling migration of mammalian cells, such as fibroblasts and neutrophils, comprising the step of exposing the mammalian cells to the novel peptide conjugates.

BRIEF DESCRIPTION OF THE DRAWINGS

FIG. 6A: Thickened stress fibers in $P34_{BSA}$-treated cells. The settings of the camera (RT Color, Diagnostic Instruments, Inc.) and the imaging software (Spot Advanced) were the same for all images. FIG. 6B: Increased mean (±standard error) fluorescence intensity of Alexa Fluor 488 phalloidin-labeled actin filaments in $P34_{BSA}$-treated fibroblasts (* P<0.05, Student's t test, n=30 randomly selected cells, 3 independent experiments).

FIG. 6C illustrates typical thickened stress fibers of $P34_{BSA}$ treated cells compared to normal thin actin filaments of maleylated $P34_{BSA}$ and control BSA treated cells. FIG. 6D illustrates Alexa fluor 488-stained actin filaments in maleylated $P34_{BSA}$-treated fibroblasts, which was not significantly different from the fluorescence intensity of the control BSA-treated cells, compared with the significantly increased fluorescence intensity for $P34_{BSA}$ treated fibroblasts (* P<0.05).

FIG. 15C illustrates the results of double labeling of Rat-2 fibroblasts for transferrin-containing endosomes and $P34_{BSA}$.

Labeling of fibroblasts for endosomes with Alexa 594-TR (left column) and for distribution of $P34_{BSA}$ by indirect immunofluorescence using Alexa Fluor 488-conjugated secondary antibody (middle column) in cells treated with control BSA (top), maleylated P34$_{BSA}$ (middle) or P34$_{BSA}$ (bottom row). Maleylated P34$_{BSA}$ was not detected. Alexa 594-TR-labeled endosomes and Alexa Fluor 488-labeled P34$_{BSA}$ did not co-localize in the merged image (right column).

Figure 16A:
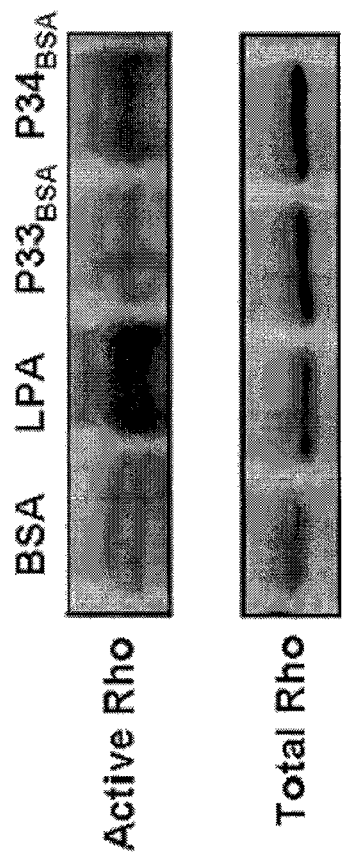
Figure 16B:
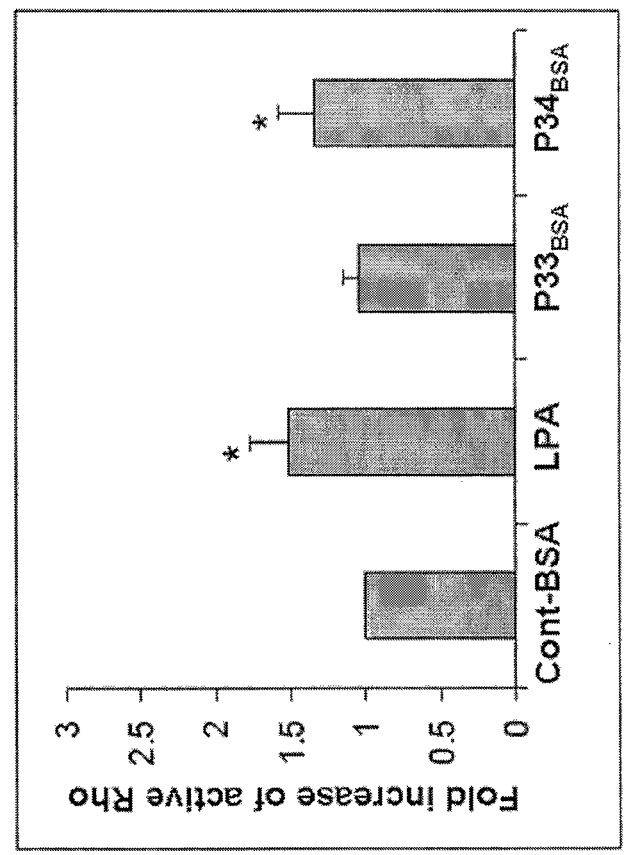

FIGS. 16A and B illustrate a Rho activity assay. FIG. 16A: Western blots of typical experiments showing activated Rho (top row) and total Rho (bottom row). FIG. 16B: Mean (± standard error) densitometric analysis of the results from three independent experiments comparing Rho activity in cells treated with BSA, positive control lysophosphatidic acid (LPA), P33$_{BSA}$ and P34$_{BSA}$.

Figure 17:
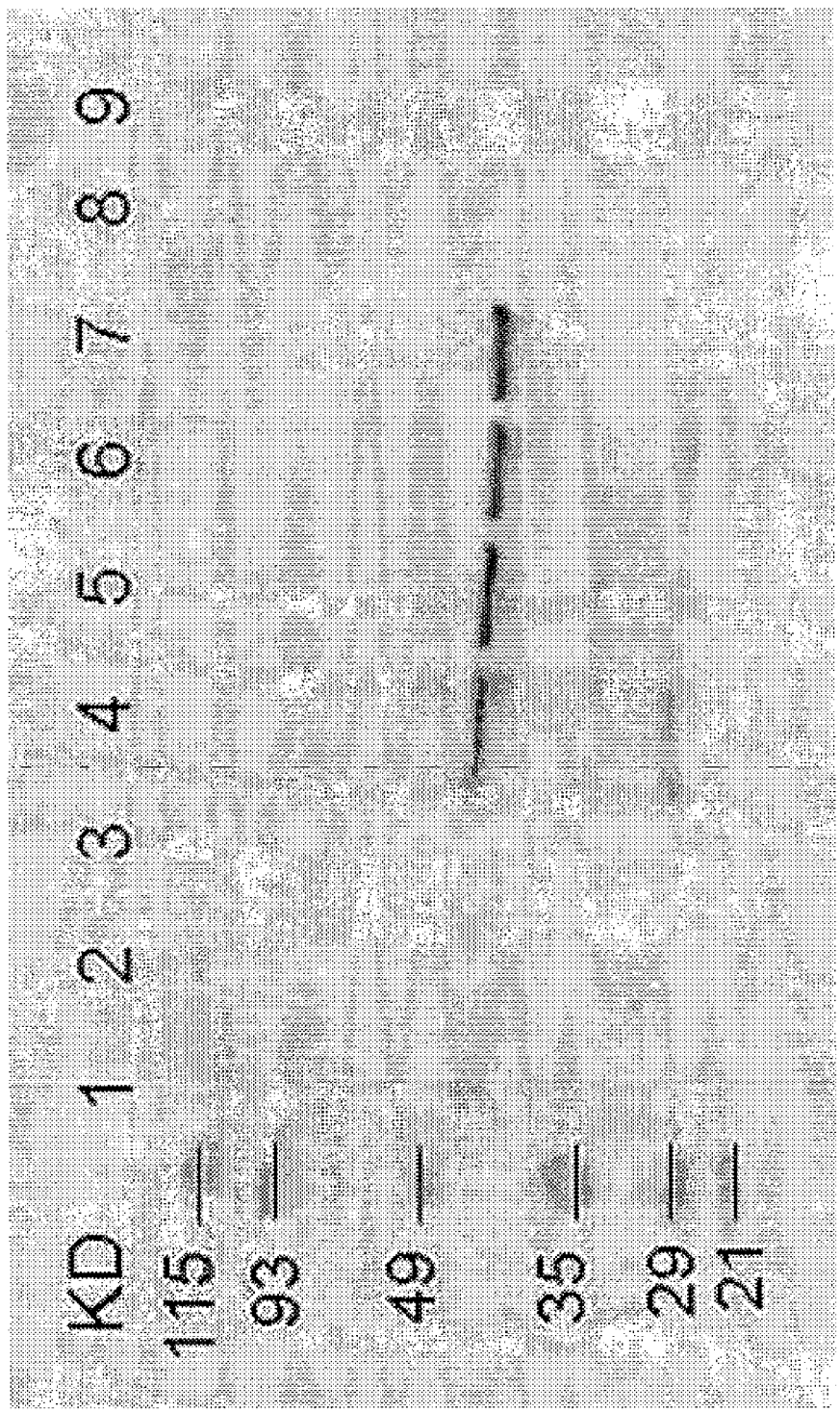

FIG. 17 illustrates Western immunoblot detection of P34$_{BSA}$ co-immunoprecipitated with actin filaments in Rat-2 fibroblast lysates. Lysates were incubated with maleylated P34$_{BSA}$ (lanes 1-3), P34$_{BSA}$ (lanes 4-6), or BSA (lanes 8,9), in the presence of phalloidin, then overnight with anti-P34 antiserum, and absorbed with protein G plus/protein A agarose beads. Absorbed proteins were separated by SDS-PAGE, transferred, and the blots were probed with anti-β-actin antibodies. Positive bands for P34$_{BSA}$ aligned with the β-actin band for the whole cell lysate (lane 7).

FIGS. 18A and 18B illustrate results of an in vitro polymerization assay. FIG. 18A: P34$_{BSA}$ did not promote polymerization of actin in the cell-free system. In the presence of 1 mM MgCl$_2$, phalloidin was able to promote polymerization of pyrene actin monomers, while P34$_{BSA}$ was not able to initiate polymerization. FIG. 18B: P34$_{BSA}$ did not inhibit actin polymerization. In the presence of actin polymerization buffer containing ATP, G-actin monomers were able to assemble themselves into F-actin, and the addition of P34$_{BSA}$ conjugate apparently did not interfere with the process.

Figure 19:
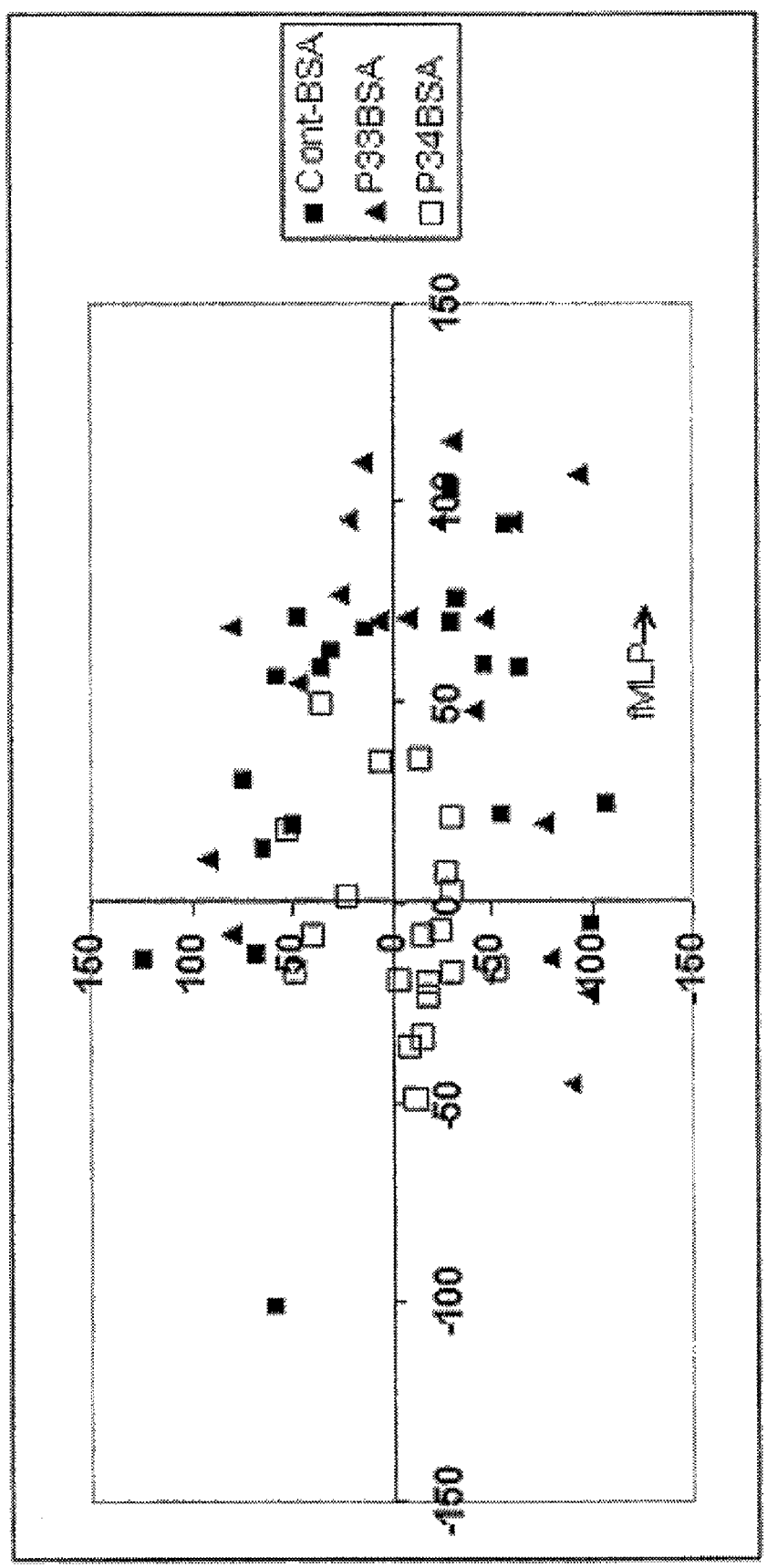

FIG. 19 illustrates reduced chemotaxis of P34$_{BSA}$-treated neutrophils in a Zygmond chamber model. The migration of the neutrophils was recorded at 20-sec intervals using time-lapse microscopy. The final position of 20 randomly selected neutrophils per group was plotted after 20 min. P34$_{BSA}$-treated cells (open squares) were disoriented compared with control BSA- (closed squares) and P33$_{BSA}$-treated cells (closed triangles), which mostly moved up the fMLP gradient.

DETAILED DESCRIPTION

In one aspect, the invention provides a peptide conjugate comprising a carrier and at least one peptide, wherein said at least one peptide has the peptide sequence YAGXDXNNXA (SEQ ID NO:1), and X is a positively charged amino acid residue. In another aspect, the positively charged residue is lysine. In yet another aspect, the carrier is bovine serum albumin.

In another aspect, the invention provides for the use of a peptide conjugate as defined above for stabilizing the actin cytoskeleton of mammalian cells.

In yet another aspect, the invention provides a method for preventing or controlling migration of mammalian cells, comprising the step of exposing said mammalian cells to the peptide conjugate as defined above.

Experimental Procedures

Generalized experimental procedures are provided herein, while additional specific details of the experiments appear in the Examples below.

Fibroblast Cell Culture

Rat-2 fibroblasts (ATCC CRL 1764) and human gingival fibroblasts (HGFs), derived from explants of healthy gingival tissue, were subcultured and grown in α-MEM containing 10% fetal bovine serum (FBS, 15% for HGFs), 100 U/ml penicillin G, and 50 µg/ml gentamicin as described previously (Pender and McCulloch, 1991; Wang et al., 2001; Batista da Silva et al., 2004; Freshney, 2005).

Polyclonal Antisera

Preimmune sera were collected from New Zealand white rabbits. The rabbits were immunized subcutaneously with 250 µg/ml of KLH-P33 or KLH-P34 in Freund's complete adjuvant and boosted at 3-week intervals. The antisera were collected 7 weeks after the second booster. The anti-peptide titers were determined by ELISA, using the BSA conjugates as antigen.

Fluorescence Microscopy of Peptide-treated Cells

The fibroblasts were grown overnight in chamber slides (Lab-Tek®, 8 well Permanox®, nunc™). The medium was aspirated and the cells were washed twice with pre-warmed α-MEM. The cells were treated with 50 µg/ml of the indicated peptide-conjugate for 1 h at 37° C. in a CO$_2$ incubator. In some experiments, cells pretreated with the peptide-conjugates were then exposed to 20 µg/ml enriched native Msp for 1 h (Wang et al., 2001). In other experiments, cells were incubated with 50 µg/ml peptide-conjugates, washed and then treated with either 0.5 µM Cytochalasin D or 1 µM Latrunculin B for 30 min at 37° C. Methods for analysis of actin filament distribution by fluorescence microscopy and fluorescence intensity by microscopic fluorimetry of Alexa Fluor 488 phalloidin (Molecular Probes)-labeled cells followed procedures described in Amin et al. (Amin et al., 2004). For analysis of de novo actin filament assembly, a rhodamine actin barbed-end incorporation assay in transiently permeabilized fibroblasts was utilized, as detailed previously (Amin et al., 2004).

EXAMPLE 1

Effect of Msp on Fibroblast Cells and Neutrophil Chemotaxis

Figure 1:
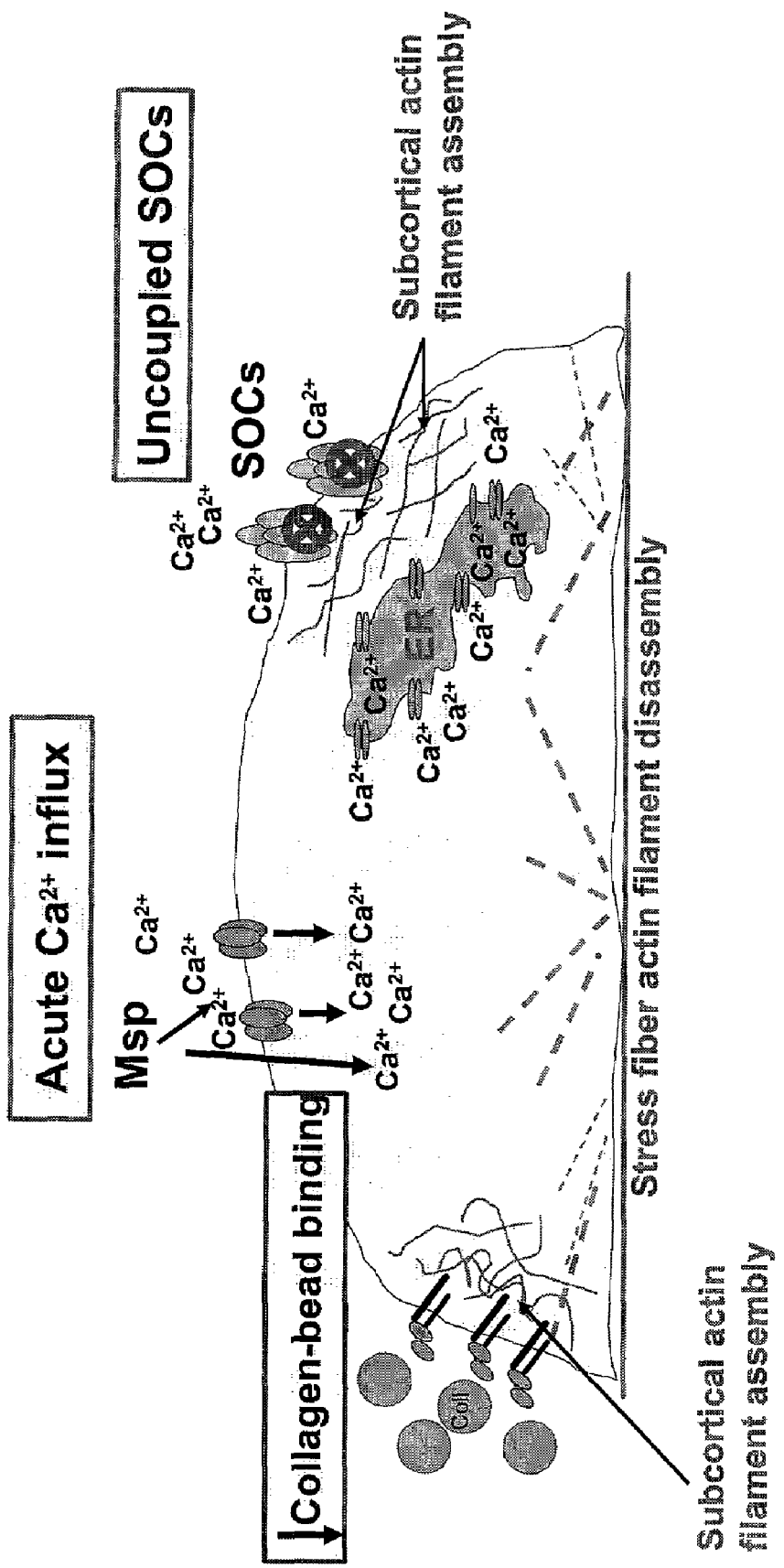
FIG. 1 illustrates how the major outer sheath protein (Msp) of *Treponema denticola* perturbs calcium flux and actin dynamics in fibroblasts.
Figure 2:
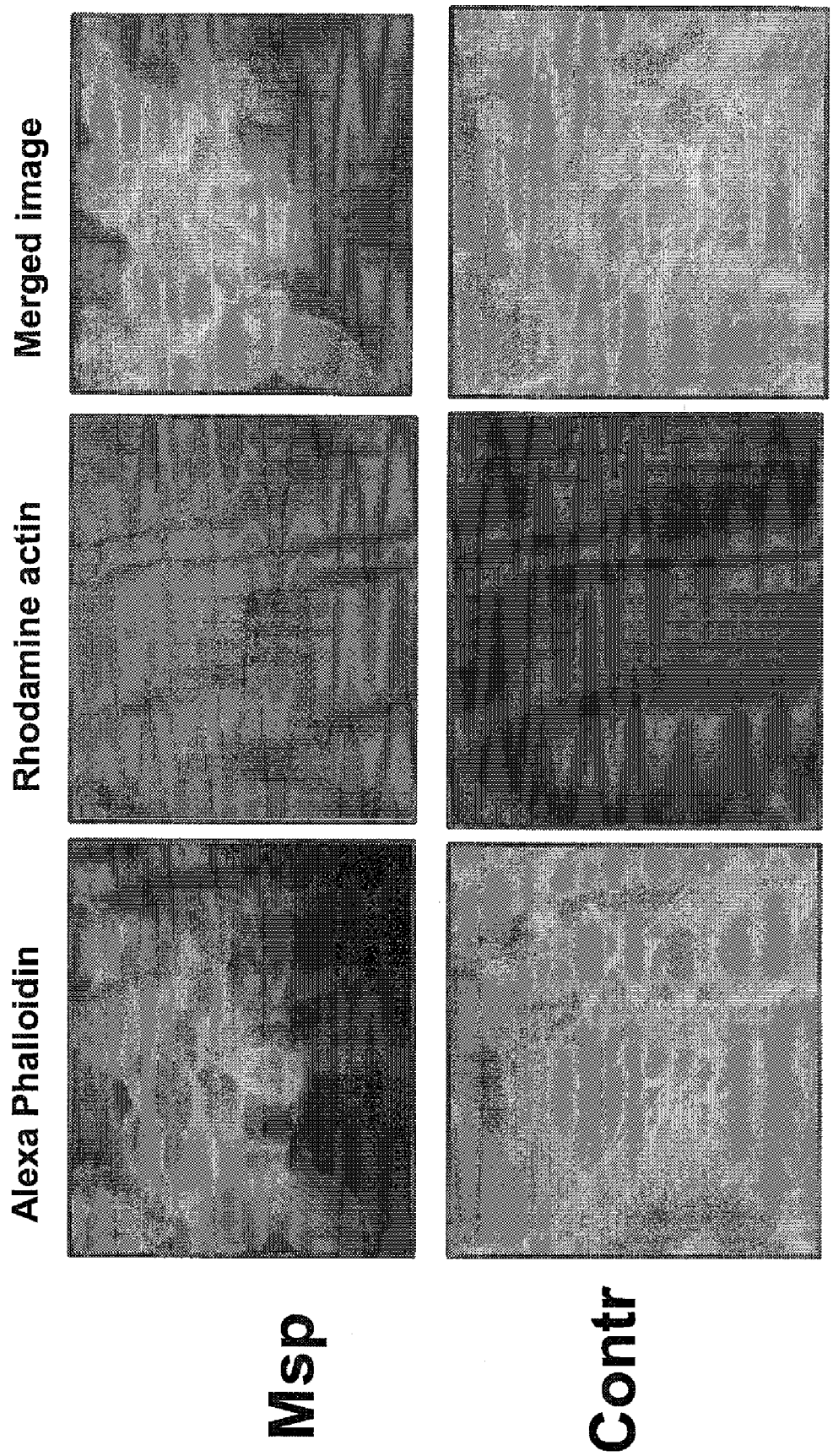
FIG. 2 illustrates the effect of Msp on actin filament reorganization in fibroblasts.
Figure 3:
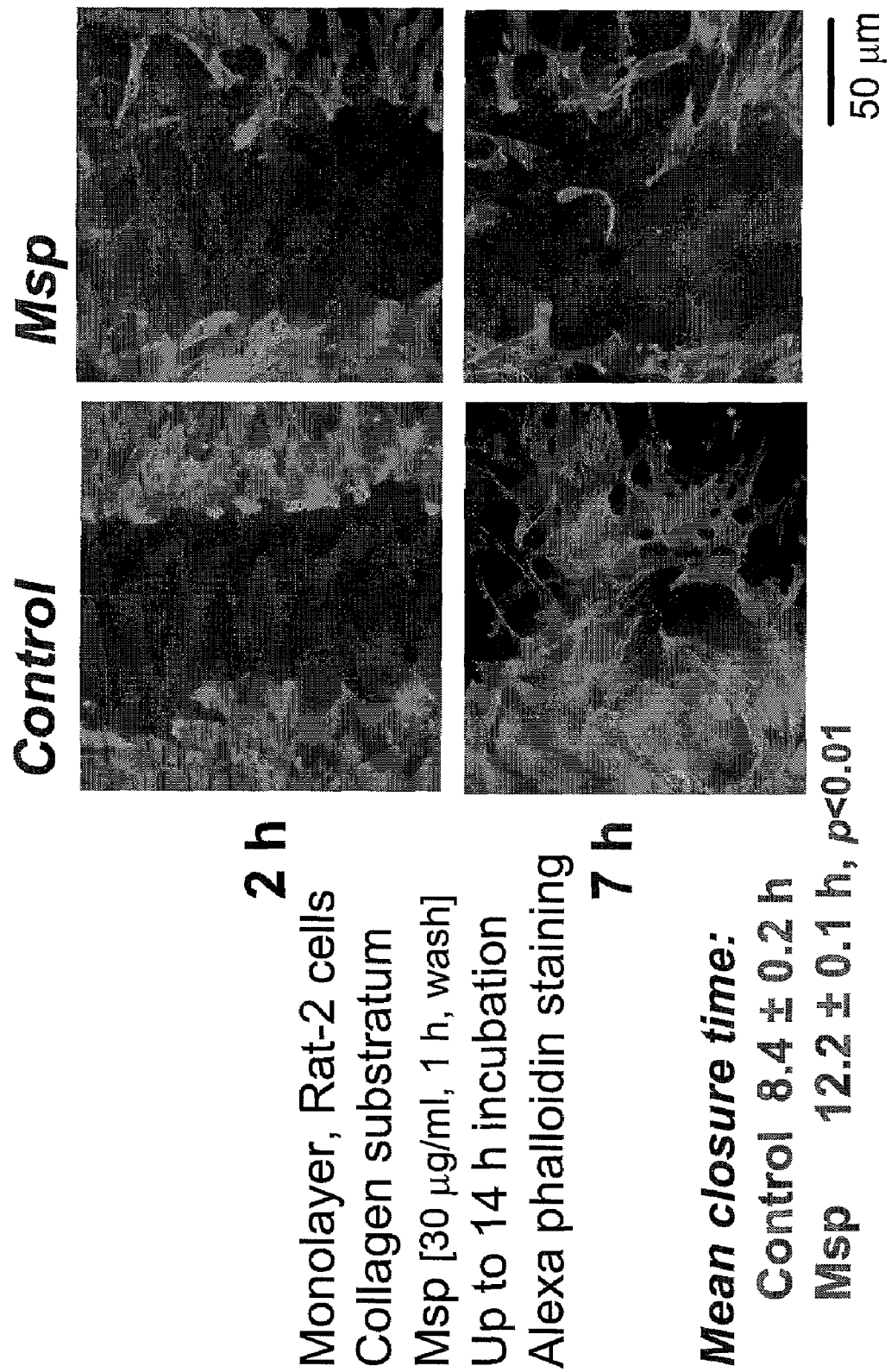
FIG. 3 illustrates the effect of Msp on the migration of fibroblast cells on a collagen matrix.
Figure 4:
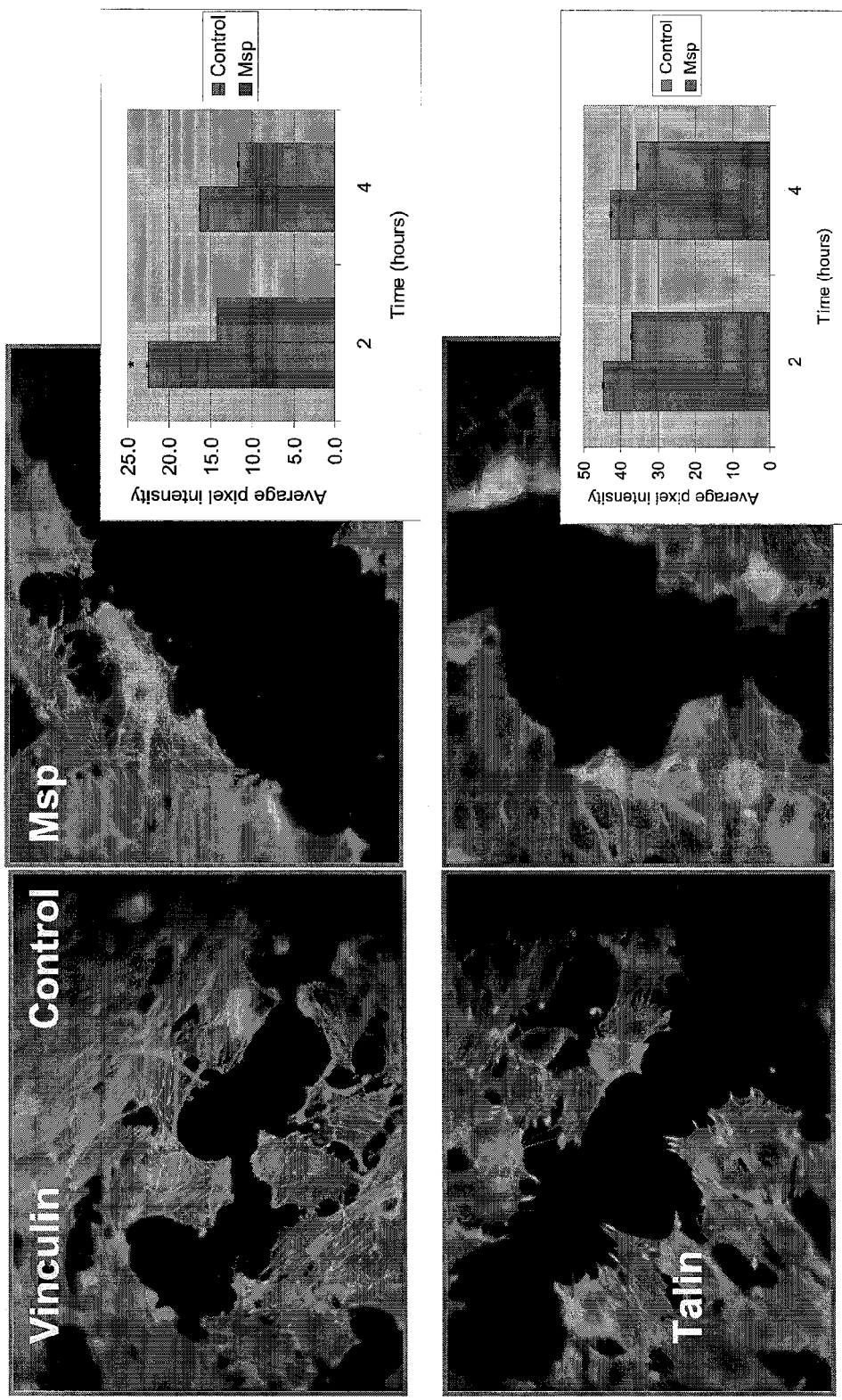
FIG. 4 illustrates the effect of Msp on the formation of focal complexes in migrating fibroblasts.

FIGS. 2 to 4 illustrate the effect of Msp on fibroblast cells.

FIG. 2. Rhodamine actin assay: As reported in Amin et al. 2004, Applicants used Rat-2 fibroblasts, which are actin filament-rich, readily cultivated, and similar to human gingival fibroblasts in many of the cytoskeletal responses that have been tested. Rat-2 cells were subcultured bi-weekly in T-25 flasks. The cells were grown to a density of 10$^4$ cells/well for 48 hours at 37° C. in a CO$_2$ incubator. The medium (α-MEM with 100 U/ml penicillin G, 50 µg/ml gentamicin, and 10% fetal bovine serum (FBS)) was changed once during this period. After obtaining 90% confluence, the medium was aspirated and the cells were washed twice with pre-warmed phosphate buffered saline (PBS) (pH 7.4). The fibroblasts were incubated with Msp (20 µg/ml) in α-MEM without serum at 37° C. in a CO$_2$ incubator for 1 h. Control cells were treated with α-MEM containing an equivalent volume of distilled water to that which was used to dilute the Msp. The fibroblasts were washed gently twice with warm PBS.

To permeabilize and to simultaneously pulse the fibroblasts with rhodamine actin monomers, the cells were exposed for 30 s to 100 µl OG buffer (10 µl 4% n-Octyl glucopyranoside diluted in 90 µl PHEM buffer, pH 6.9, containing 6 mM PIPES, 2.5 mM HEPES, 1 mM EGTA, 0.2 mM MgCl$_2$, 0.1 mM ATP, and 0.23 mM rhodamine actin). Permeabilization of the fibroblasts was stopped by adding 300 µl of buffer B (5 mM β-mercaptoethanol, 1 mM Tris base, 1 mM EGTA, 2 mM MgCl$_2$, 10 mM KCl, 5 mM ATP, pH 7.4) for 2 min at 37° C. The buffer was removed and the cells were fixed with 3.7% formaldehyde for 10 min. The cells were washed with PBS four times. Two hundred μl of 0.1% Triton X-100 was added to the wells; after 5 min, the cells were washed 3 times. Alexa Fluor 488 phalloidin was added to the wells for 20 min, and the cells were then washed 3 times. The chamber and gasket were removed, and the slide was covered with anti-fade mounting fluid and a coverslip. Fluorescence microscopy at a magnification of 40× (Zeiss Universal Research Microscope, Germany) was used to produce images of cells stained with rhodamine actin (excitation light BP546/12, emission filter LP 590, FT 580 chromatic beam splitter) and Alexa Flour 488 phalloidin (exitaion light 420, emission filter BP520-560, FT510 chromatic beam splitter). The images obtained from the two channels were merged with Photoshop® software.

Dual labeled fluorescent images of Msp-treated fibroblasts showed an intense band of subcortical rhodamine actin fluorescence co-localized with Alexa Fluor phalloidin stained filaments along the periphery of the cells, and detected contemporaneous stress fiber disruption toward the center of the cells. Msp-treated cells became oval in shape. In contrast, the control vehicle-treated cells maintained their stellate shape, and co-localized fluorescence was limited to discreet focal complexes at the plasma membrane. In Msp-treated cells, there was a significant decrease in the ratio of centrally distributed Alexa Fluor phalloidin fluorescence intensity to subcortical fluorescence intensity ($p<0.001$), indicating that disassembly of actin filaments toward the center of the cell occurred contemporaneously with de novo subcortical actin filament assembly. The concomitant increase in peripheral rhodamine actin fluorescence intensity in the Msp- relative to the vehicle-treated cells ($p<0.05$) confirmed that exposure of fibroblasts to Msp led to elongation of actin filaments at their fast growing barbed end.

FIG. 3. In vitro fibroblast migration model: As reported in Amin et al., 2004, Applicants investigated the effect of Msp treatment on the migration of fibroblasts across a type 1 collagen substratum to close a narrow "wound" line in the cell monolayer. Msp-pretreated (20 μg/ml, 1 h, followed by washing) and vehicle-treated Rat-2 cells were grown to confluence. A sterile needle was drawn across the monolayer to create a wound. The migration of cells at the periphery to close the wound was observed hourly for 14 h. Msp pretreatment had a significant inhibitory effect on the migration of the fibroblasts. Migration of the control cells covered the wound gap 50% faster than that of the Msp-pretreated cells (8.4±0.2 h versus 12.2±0.1 h, respectively, $p<0.01$, n=3 experiments).

FIG. 4. Focal adhesion vinculin in migrating fibroblasts: Confluent Rat-2 fibroblasts were pretreated with either 20 μg/ml Msp or Msp-free α-MEM vehicle control for 1 h. An incision was created in the monolayer using a sterile needle. The cells were incubated for different intervals up to 12 h. Cells were permeabilized, then stained with Alexa 488 phalloidin for actin filaments and by indirect immunofluorescence with an Alexa 594 conjugate for the actin-binding protein vinculin. Protein localization was recorded in merged images. Fluorescent pixel intensity was measured among cells along the wound edge. Results: There was a significant delay in wound closure ($P<0.05$). At early times, Msp-pretreated cells had altered shape and loss of focal distribution of vinculin. Yet, mean pixel intensity along the wound edge was significantly lower in Msp-treated than control cells only for vinculin at 2 h (% difference=37%; P=0.003). There were no significant differences for vinculin beyond 2 h. It was concluded that exposure of rat-2 fibroblasts to Msp delays cell migration to close wounds. Distributional change of the actin-binding protein vinculin away from discrete focal adhesions may contribute to Msp-induced reduction of collagen-binding affinity of integrins.

Figure 5:
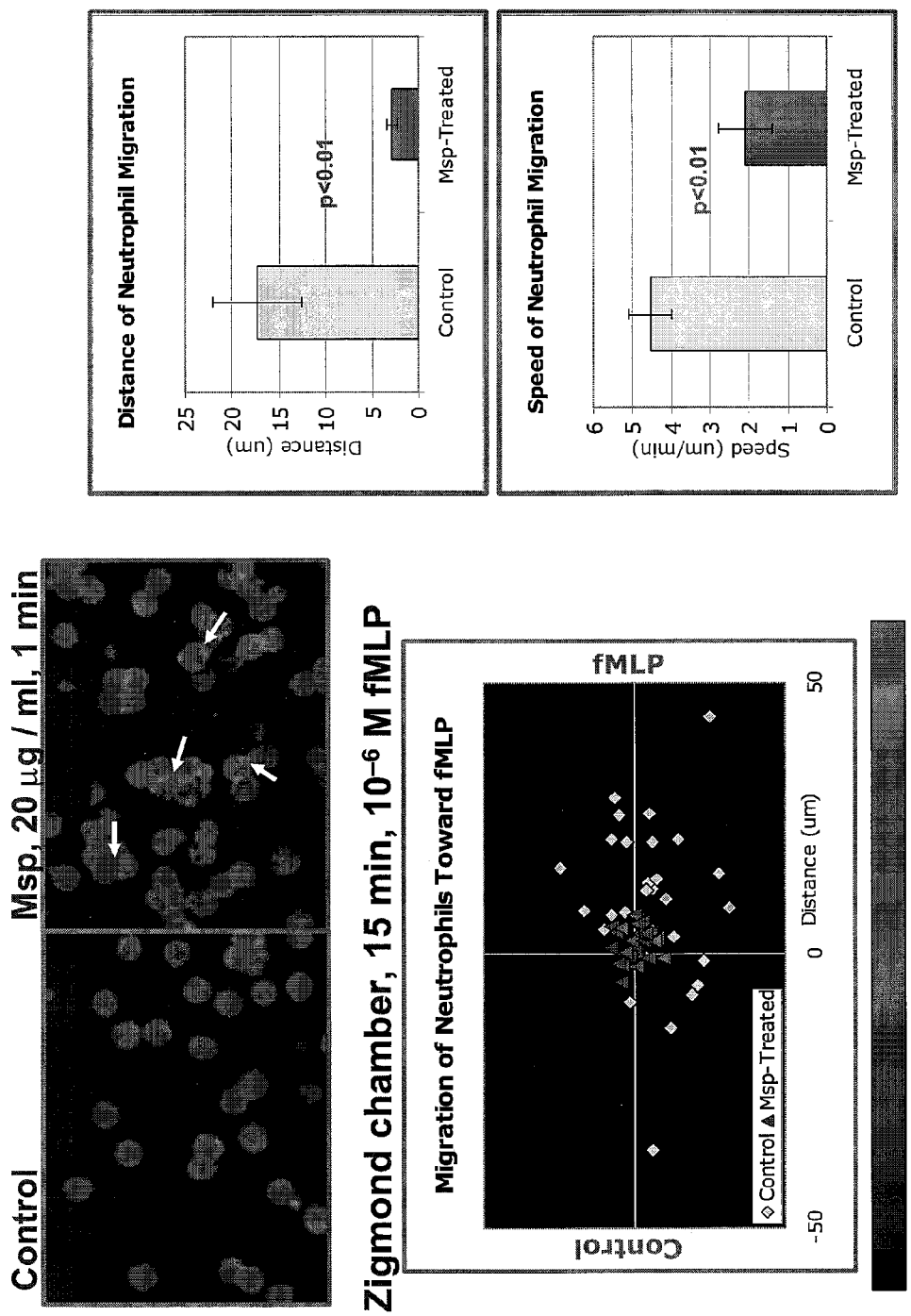
FIG. 5 shows how Msp inhibits neutrophil chemotaxis toward fMLP.

It has been shown before by Applicants that Msp induces coincident loss of stress fibers and de novo subcortical actin filament assembly in fibroblasts (Amin et al., 2004). Applicants reported (Amin et al., 2004) and recently confirmed that Msp inhibits neutrophil chemotaxis. Applicants also found that Msp inhibits phagocytosis and affects actin assembly and calcium transients in neutrophils exposed to a chemoattractant, without inducing apoptosis in the neutrophils (Thomas et al., 2006, accepted for publication in Infection and Immunity). FIG. 5 illustrates that Msp inhibits neutrophil chemotaxis toward a well known chemoattractant fMLP FIG. 5. To assay chemotaxis, Msp-pretreated (20 ug/ml, 30 min) and control murine neutrophils were localized on the bridge of a Zigmond chamber. 15 min migration direction, distance, and speed in response to the chemoattractant fMLP, N-formyl-methionyl-leucyl-phenylalanine tripeptide ($10^{-6}$M) were recorded digitally. Msp-treated neutrophils failed to migrate toward fMLP, (Control 17.3±4.8; Msp-treated 2.8±0.7 $p<0.01$). Moreover, the movement occurred at a reduced speed (Control 4.5±0.6; Msp-treated 2.1±0.7 $p<0.01$). Conclusions: The Msp of *Treponema denticola* inhibits chemotaxis of neutrophils. It also reduces the speed of neutrophil locomotion.

Rhodamin actin staining (illustrated in FIG. 2) revealed that many of the neutrophils exposed to Msp for 1 min and examined by fluorescence microscopy showed a much brighter band of rhodamine fluorescence in the cell periphery than the fluorescence of cells exposed to the vehicle control. Same effect was observed in the fibroblasts treated with Msp (Amin et al., 2000)

Thus, it is clear from the teachings of the prior art and the foregoing experiments that Msp exerts significant effects on the actin cytoskeleton and on the migration of mammalian cells.

EXAMPLE 2

Design and Synthesis of Peptide-BSA Conjugates

Applicants conducted a bioinformatics analysis and computational investigation of the Msp deduced amino acid sequence that was deposited in NCBI by Fenno et al., 1996. The genome sequence of *T. denticola* has also been published in PNAS (Seshadri et al., 2004).

The Msp amino acid sequence was compared with the surface antigens and secretory toxins of other pathogenic bacteria in the database. Also, the MacVector® program (Accelrys Software Inc.) was used to determine the regions of the Msp deduced amino acid sequence that would have high probability of surface exposure and antigenicity. MacVector® was used to determine surface exposure regions. This program was designed to predict which regions of a protein are most likely to be positioned on the protein's surface, based on knowledge of which amino acids are more likely to be found on the surface of proteins of known structure. MacVector® uses its own formula. This program sums the seven fractional probabilities of the amino acids in the window and divides by six to yield a running average of the fractional surface probability along the length of the protein. Thus, a value of 1 at any point would mean that a heptapeptide centered about that point is definitely exposed at the surface of the protein and a value of 0.0 means that the heptapeptide is definitely buried in the interior of the protein.

One of the criteria that this program uses for calculating the surface probability is hydrophilicity. Each of the 20 amino acids is assigned a hydropathy value based on previous experimental or empirical measures. A window of 7 amino acids is run along the length of the protein; for each window, the hydropathy values of the 7 amino acids are summed and divided by 7 to obtain the average hydrophilicity per residue for the window. The value is then plotted on the graph at the center of the window. Values above the cut-off denote hydrophilic regions which may be exposed on the outside of the molecule; values below the cut off indicate hydrophobic regions which tend to be buried inside the molecule or inside other hydrophobic environments such as membranes. Various amino acid hydropathy scales have been developed for hydrophilicity profile. The Kyte-Doolittle (1982) scales were originally used for hydrophobicity profiles; so the peaks are reversed to get the hydrophilicity plot instead. Among the Msp domains, four domains with putative surface exposure were selected for further study, and 10-mer peptides that were part of these domains were synthesized commercially by placing orders to Alberta Peptide Institute (University of Alberta, Edmonton, Alberta), which supplied keyhole limpet hemocyanin (KLH)-conjugates for immunizing rabbits, bovine serum albumin (BSA)-conjugates for use in biological assays and immunoassays to test the titer once Applicants obtained the rabbit antiserum, and the free peptides. The sequences of the four peptides are as follows:

$P31_{BSA}$: BSA-$^{81}$LGVNLAYRFY$^{90}$-(SEQ ID NO:3), BSA: peptide ratio, 1:18

$P32_{BSA}$: BSA$^{222}$GATYYKQNGI$^{231}$-(SEQ ID NO:4), BSA: peptide ratio, 1:18

$P33_{BSA}$: BSA-$^{319}$GSNPDKPYLG$^{328}$-(SEQ ID NO:5), BSA: peptide ratio, 1:6

$P34_{BSA}$:BSA-$^{385}$YAGKDKNNKA$^{394}$-(SEQ ID NO:1), BSA: peptide ratio, 1:6

Brief outline of the methods to synthesize and analyze the peptide conjugates [from product information supplied by Alberta Peptide Institute]: The Alberta Peptide Institute uses a coupling reagent, benzoyl benzoic acid, to couple peptides to BSA. This reagent is added to the peptide at the N-terminal free amino function during peptide synthesis. Peptides are coupled to BSA by photolysis for one hour in phosphate buffered saline (PBS). The solution is dialysed to remove uncoupled peptide and buffer. Upon conjugation, more than one peptide attaches to the carrier so it would be expected to have multivalency. The ratio of conjugation for control peptide P33 and the peptide of interest, P34, is 6:1 (peptide/BSA) The ratio of conjugation for P31 and P32 is 18:1. The peptides are purified by HPLC. Amino acid composition is determined using a Beckman 6300 amino acid analyzer, and molecular weights are determined by electrospray mass spectrometry.

Other methods for conjugating peptides to BSA carriers are commonly known and may be employed by those skilled in the art.

EXAMPLE 3

Effect of Peptide Conjugate $P34_{BSA}$ on Actin Cytoskeleton of Fibroblasts

Figure 6A:
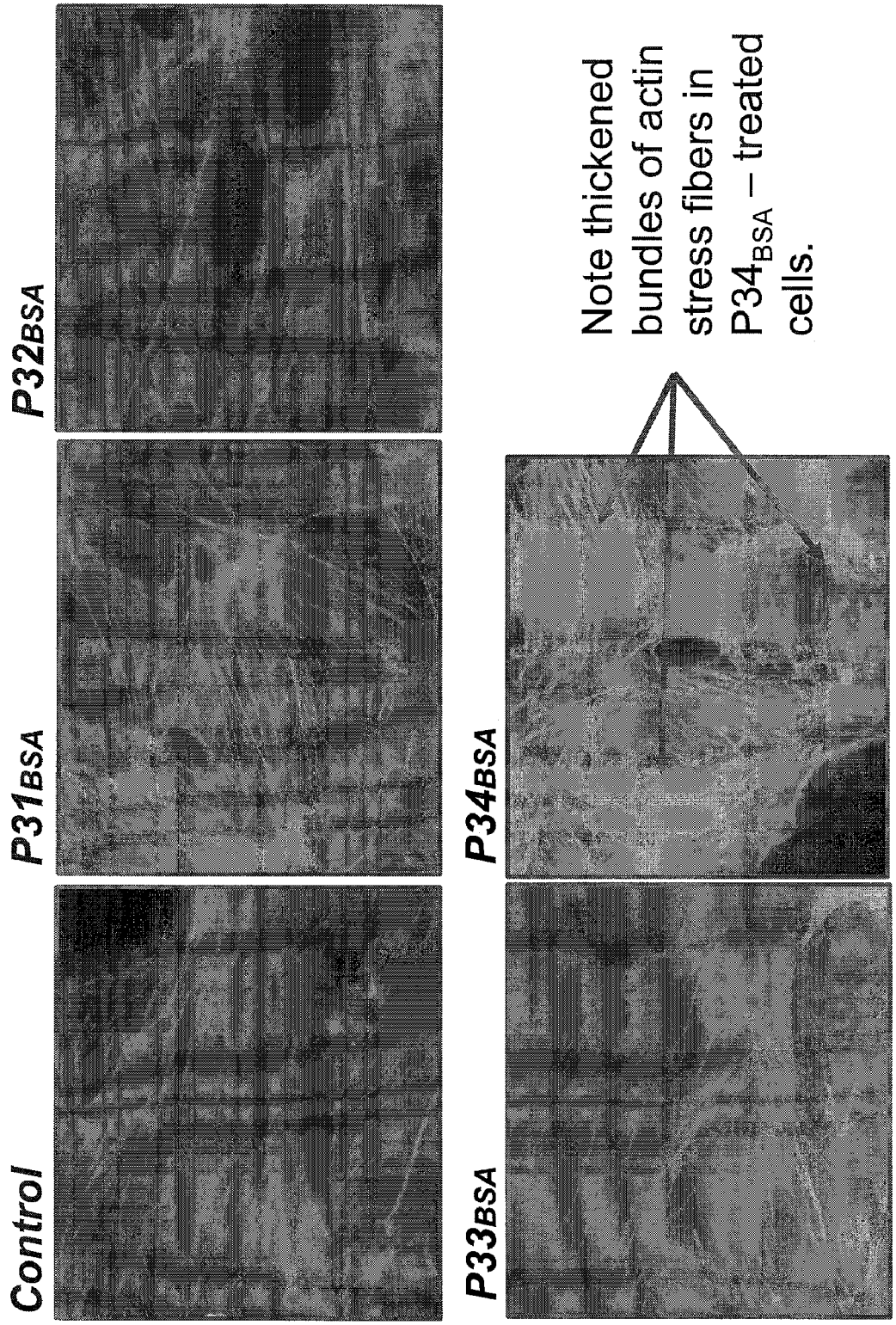
FIGS. 6A and 6B illustrate the results of experiments where Rat-2 fibroblasts were exposed to various BSA-peptide conjugates.
Figure 6B:
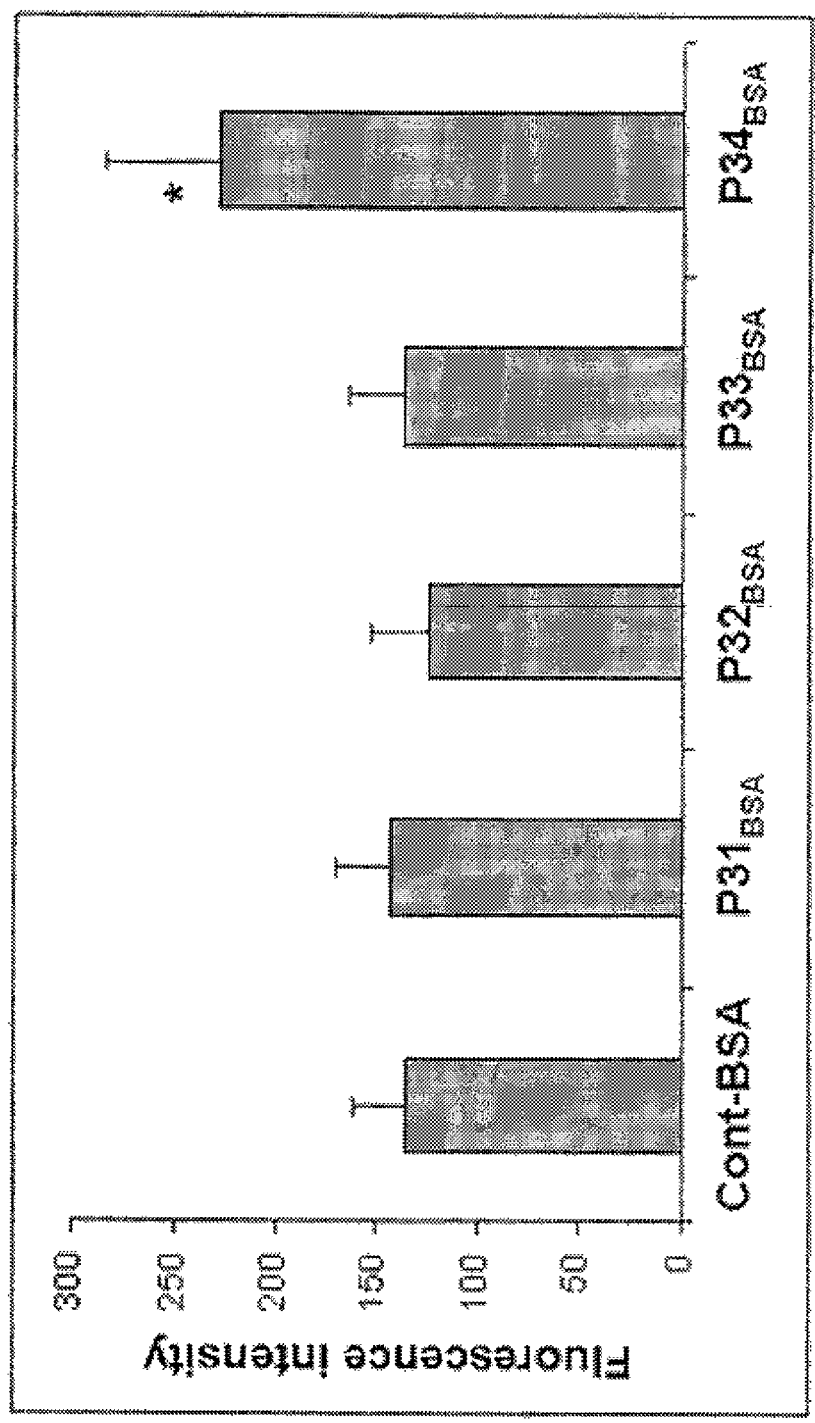

One of the peptide-BSA conjugates, designated $P34_{BSA}$, when exposed to both human gingival fibroblasts and rat-2 fibroblasts, caused the cells to produce thicker actin stress fibers (see FIGS. 6A and 6B). The experiment in FIGS. 6A and 6B was carried out with permeabilized rat-2 fibroblasts. The cells were treated with 50 µg/ml of the indicated peptide conjugates for one hour at 37° C. in a $CO_2$ incubator. The cells were washed with 0.01 M PBS and fixed with formaldehyde 3.7%. The actin stress fibers were stained with 0.165 µM Alexa Fluor 488 Phalloidin for 20 minutes). As previously mentioned, the sequence of the synthetic peptide that is conjugated to BSA in the $P34_{BSA}$ conjugate is YAGKDKNNKA (SEQ ID NO:2). The intensity of the fluorescence staining of actin filaments was quantified by Image ProPlus software. The quantification of the staining showed that the $P34_{BSA}$ treated fibroblasts had a greater mean fluorescence intensity than both control cells that had been treated with BSA and fibroblasts treated with the other peptide conjugates. The same result was observed in human gingival fibroblasts (HGFs; data not shown). The free peptide, P34, lacked this activity.

To determine whether the cationic nature of P34 could account for its activity, $P34_{BSA}$ was treated with maleic anhydride, according to Work and Burdon (Work and Burdon, 1980), to block the amino side groups of its 3 lysine residues. The peptide was dissolved in 0.2 M phosphate buffer, pH 8.5. The solution was cooled on ice to 0-2° C. and maintained at this temperature throughout the reaction. Solid maleic anhydride was added in small aliquots to the solution, which was stirred and maintained at pH 8.5-9.0 by the addition of 4 N NaOH. The final concentration of added reagent was 0.1 M. When the lack of base uptake indicated the end of the reaction, the solution was dialyzed against 0.01 M PBS, pH 7.4. The concentration of protein in the dialysate was measured by using the Bio-Rad protein assay kit (Bio-Rad Laboratories, Inc.).

Figure 6C:
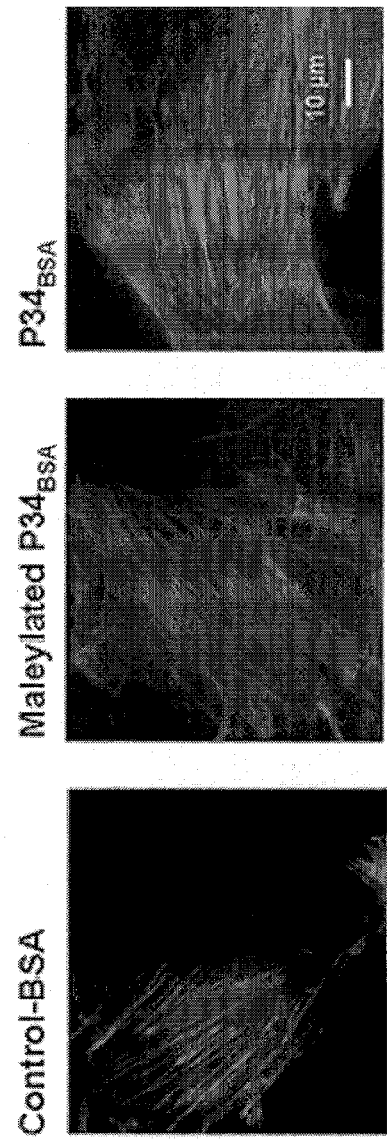
FIGS. 6C and 6D illustrate the results of experiments where $P34_{BSA}$ conjugate was treated with maleic anhydride.
Figure 6D:
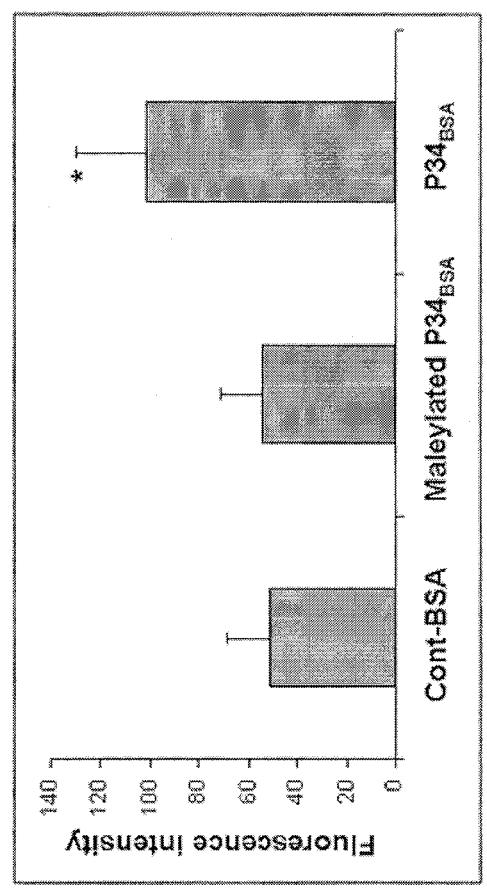

Maleic anhydride treatment of $P34_{BSA}$ neutralized its impact on the thickness of the stress fibers in Rat-2 fibroblasts. Maleylated $P34_{BSA}$-treated cells had normal, uniformly thin actin filaments, similar to control BSA-treated cells (FIGS. 6C and 6D).

EXAMPLE 4

Figure 7A:
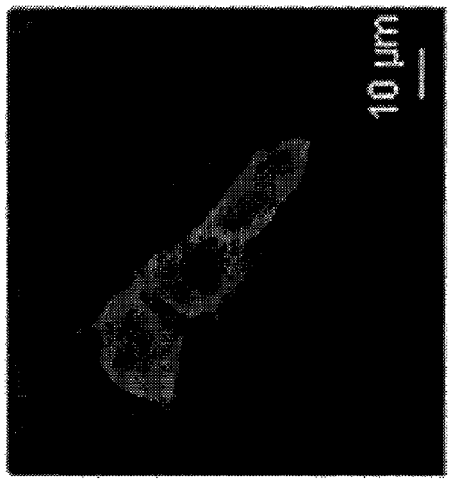
FIG. 7a compares the effect of pretreatment with the active peptide conjugate containing the sequence YAGKDKNNKA (SEQ ID NO:2), $P34_{BSA}$, and a control peptide in the Msp sequence, $P33_{BSA}$, on Msp-induced actin filament reorganization of fibroblast cells. Pretreatment with $P34_{BSA}$ protects Rat-2 fibroblasts from Msp-induced actin filament reorganization (bottom row) compared with pretreatment with the control peptide conjugate $P33_{BSA}$ (top row). A Rhodamine actin incorporation assay that labels the rapidly growing barbed end of actin filaments showed that Msp caused the formation of a meshwork of subcortical actin filaments in the control $P33_{BSA}$-pretreated but not the $P34_{BSA}$ pretreated cells (right column), which is the typical effect of Msp on host cells (Amin et al, 2004).
Figure 7A:
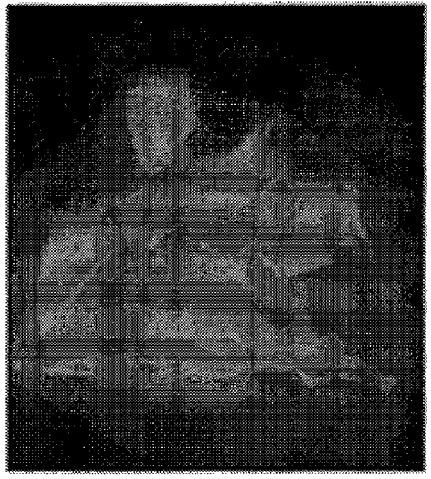
Figure 7A:
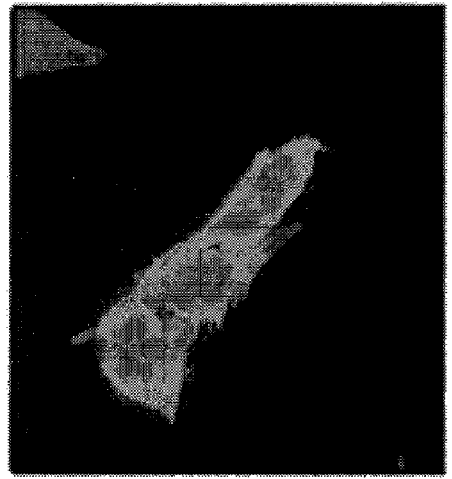
Figure 7B:
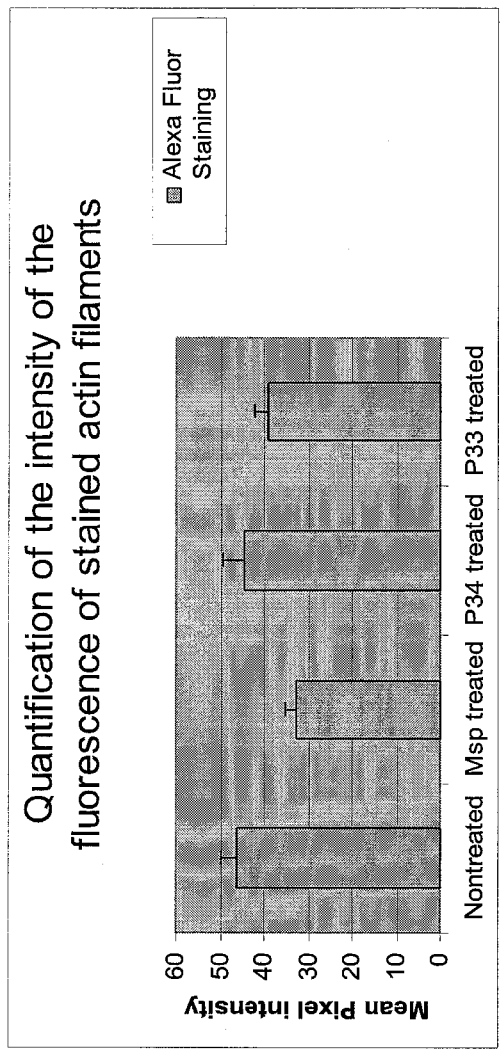
FIG. 7b quantifies the intensity of the fluorescence of stained actin filaments and FIG. 7c illustrates the measurement of the surface area of the fibroblasts pretreated with the peptide conjugates and subsequently treated with Msp. Pretreatment with $P34_{BSA}$ but not control $P33_{BSA}$ maintained the surface area of fibroblasts upon subsequent exposure to Msp. (* P<0.05).
Figure 7C:
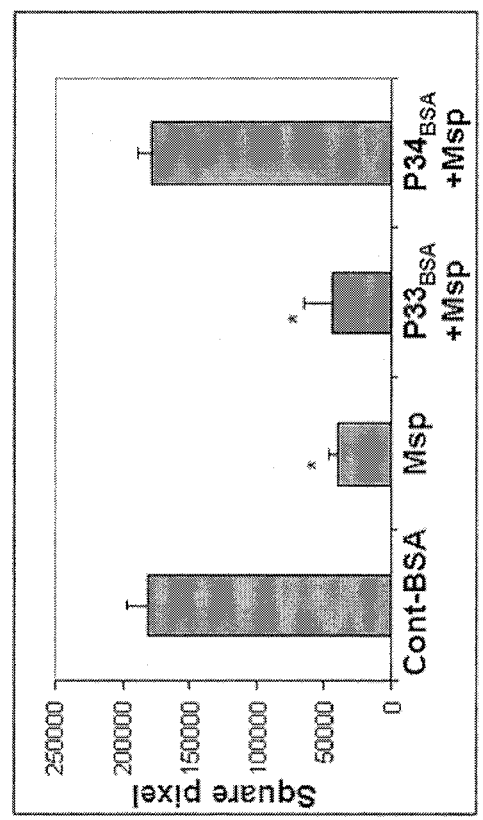

Effect of Pretreatment of Fibroblasts with $P34_{BSA}$ Conjugate on Msp-induced Actin Filament Reorganization A reproducible and readily quantifiable functional outcome of Msp-induced stress fiber disruption in fibroblasts is their retraction from a spread, stellate shape, which is reflected in a decrease in surface area (Batista da Silva et al., 2004). Pretreatment of the fibroblasts with $P34_{BSA}$ conjugate, but none of the other peptide conjugates, maintained their surface area upon exposure to Msp. The control peptide conjugate $P33_{BSA}$ had no such effect. Pretreatment with $P34_{BSA}$ also protected the actin cytoskeleton. FIG. 7a compares the effect of pretreatment with $P34_{BSA}$ and $P33_{BSA}$ conjugates on Msp-induced actin filament reorganization of fibroblast cells. A rhodamine actin incorporation assay was used to locate cytoplasmic compartments where there was intense de novo actin filament assembly (Amin et al., 2004). The Rhodamine actin assay revealed that Msp (20 µg/ml) disrupted actin filaments in cells pretreated with control peptide $P33_{BSA}$ (50 µg/ml) but not in cells pretreated with $P34_{BSA}$ (50 µg/ml). Dual-labeled fluorescent images of control $P33_{BSA}$-pretreated fibroblasts showed an intense band of subcortical rhodamine actin fluorescence co-localized with Alexa Fluor phalloidin-stained filaments around the periphery of the cells, and detected coincident stress fiber disruption. The cells became oval in shape. In contrast, the $P34_{BSA}$-treated cells had little evidence of rhodamine incorporation subcortically and they maintained their stellate shape. FIG. 7a illustrates that $P34_{BSA}$ pretreatment protected the fibroblasts from the usual actin-perturbing effect of Msp, as illustrated in FIG. 2. The bar graphs in FIGS. 7b and 7c show the quantification of the stained cells which were pretreated with P34$_{BSA}$ conjugate and control peptide conjugate P33$_{BSA}$ for one hour, washed, and subsequently exposed to Msp for one hour. The measurement of fluorescence intensity (FIG. 7b) and the surface area of the fibroblasts (FIG. 7c) showed that P34$_{BSA}$ pretreatment maintained the fluorescence intensity and surface area of the cells upon exposure to Msp. The experiments revealed that pretreatment with P34$_{BSA}$ conjugate protected the fibroblasts from the actin filament disassembly and cell shrinkage upon exposure to Msp, while P33$_{BSA}$ conjugate pretreated cells depolymerized and reorganized their actin stress fibers (lower staining intensity) and rounded up (diminished cell surface area) when treated with Msp.

EXAMPLE 5

Figure 8A:
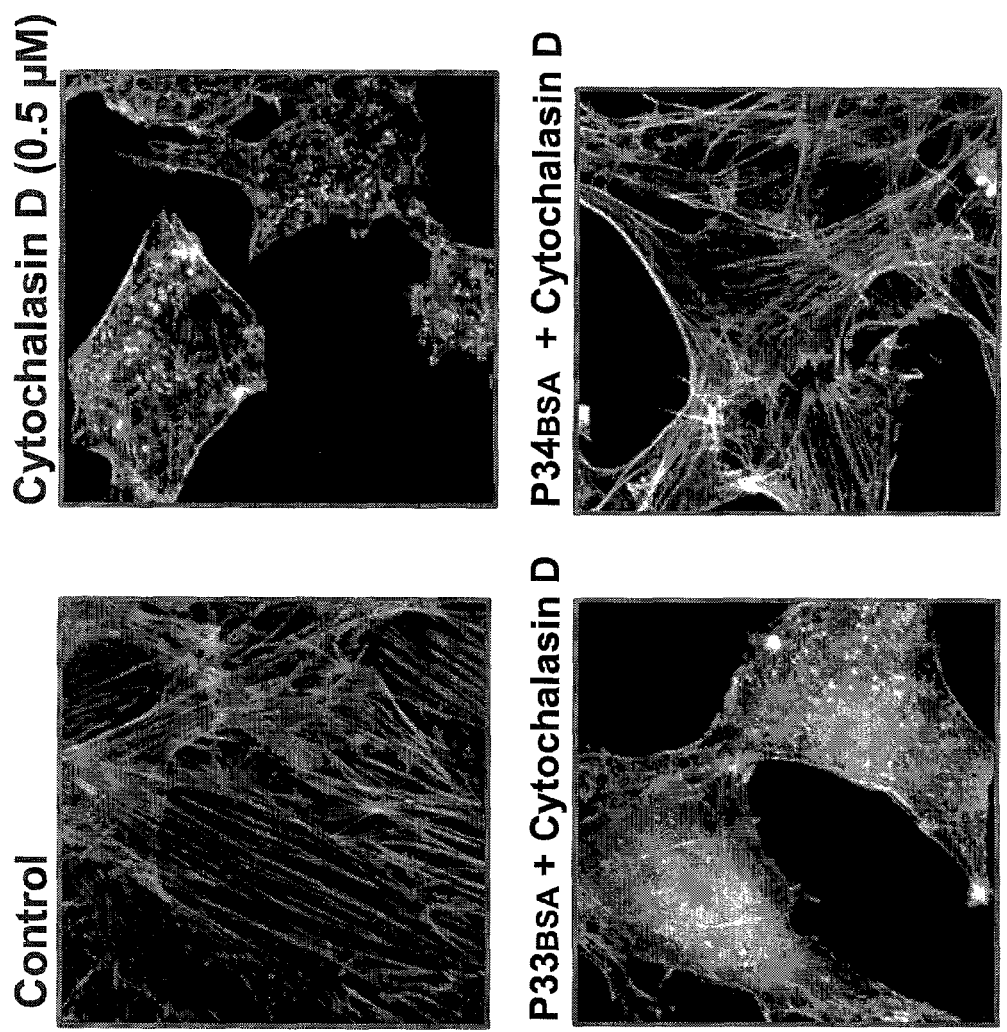
FIG. 8A illustrates the effect of pretreatment with $P34_{BSA}$ and $P33_{BSA}$ conjugates on Cytochalasin D-mediated inhibition of actin assembly in fibroblast cells.
Figure 8B:
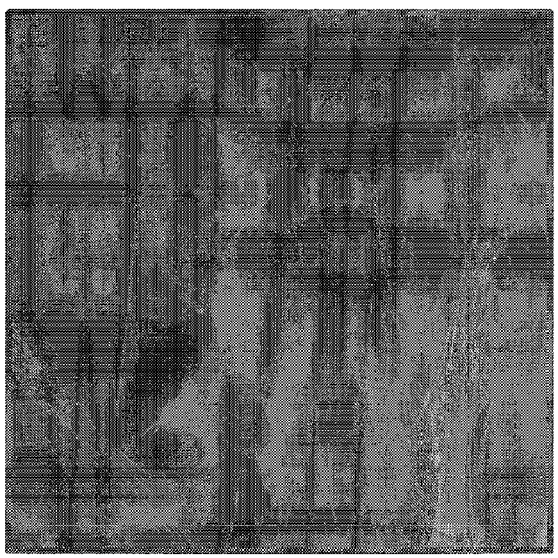
FIG. 8B illustrates the effect of pretreatment with $P34_{BSA}$ and $P33_{BSA}$ conjugates on Latrunculin B-mediated inhibition of actin assembly in fibroblast cells.
Figure 8B:
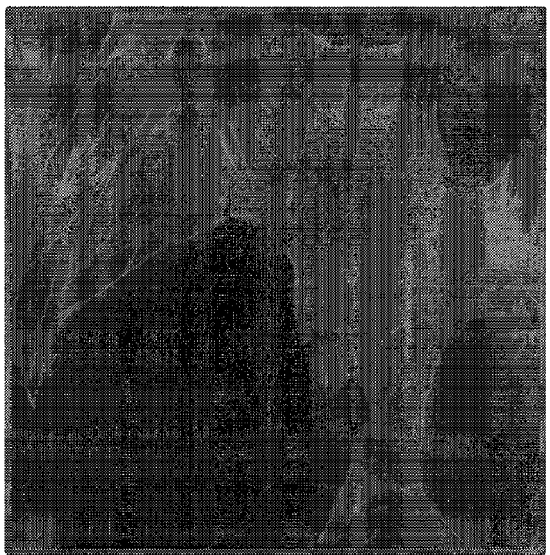
Figure 8B:
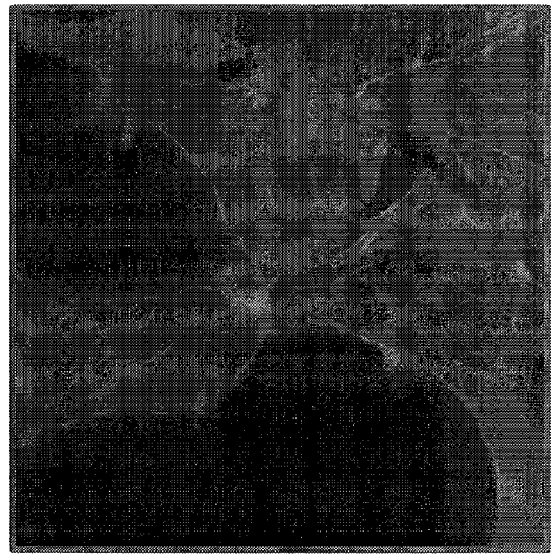

Effect of Pretreatment of Fibroblasts with P34$_{BSA}$ Conjugate on Cytochalasin D- and Latrunculin B-mediated Actin Inhibition Applicant then sought to determine whether the actin stabilizing properties of P34$_{BSA}$ were specific for *T. denticola* Msp or if P34$_{BSA}$ could protect cells from commonly used actin inhibitors, such as Cytochalasin D and Latrunculin B. Indeed, pretreatment of cells with P34$_{BSA}$ conjugate protected them from conventional doses of these two agents in a concentration-dependent manner (FIGS. 8 and 9). FIG. 8A illustrates the effect of pretreatment with P34$_{BSA}$ and P33$_{BSA}$ conjugates on Cytochalasin D-mediated inhibition of actin assembly in fibroblast cells. FIG. 8B illustrates the effect of pretreatment with P34$_{BSA}$ and P33$_{BSA}$ conjugates on Latrunculin B-mediated inhibition of actin assembly in fibroblast cells. The fibroblasts were pretreated with 50 µg/ml of either P34$_{BSA}$ conjugate or P33$_{BSA}$ conjugate for one hour in the $CO_2$ incubator at 37° C. Then the cells were washed with PBS buffer to remove the unbound peptide conjugates. Afterwards the cells were exposed to either Cytochalasin D or Latrunculin B. FIG. 8A shows the cells that were subsequently treated with 0.5 µM Cytochalasin D for 30 minutes, and FIG. 8B illustrates the cells that were subsequently exposed to 1 µM Latrunculin B for 30 minutes. Then, the cells were fixed and stained with Alexa Fluor 488 Phalloidin as previously described.

Figure 9B:
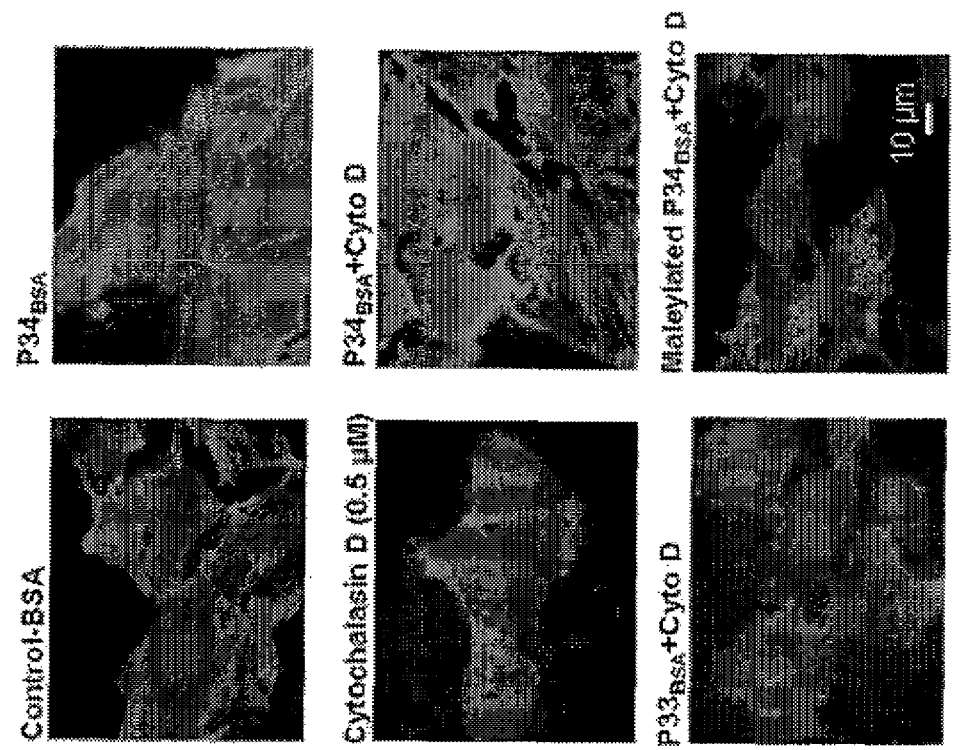
FIG. 9A and FIG. 9B further illustrate that pretreatment with $P34_{BSA}$ protected the cytoskeleton of Rat-2 fibroblasts from Cytochalasin D and Latrunculin B. Fibroblasts were pretreated with either $P33_{BSA}$, $P34_{BSA}$, or maleylated $P34_{BSA}$, washed, and then exposed to 1 μM Latrunculin B (9A) or 0.5 μM cytochalasin D (9B) for 30 min, prior to labeling with Alexa Fluor 488 phalloidin. Note thick stress fibers in $P34_{BSA}$-pretreated cells, similar to FIG. 6A. $P34_{BSA}$ pretreated cells were partially protected against the actin filament disrupting effects of cytochalasin D and latrunculin B compared with the completely disrupted actin filaments in $P33_{BSA}$- or maleylated $P34_{BSA}$-pretreated cells.
Figure 9A:
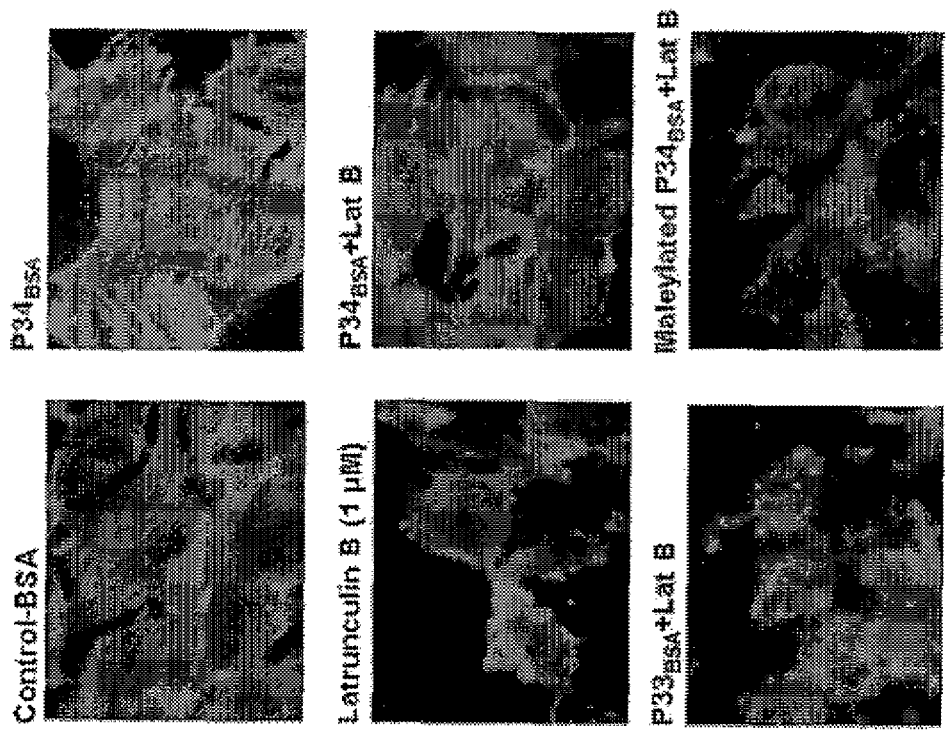

FIGS. 9A and 9B illustrate the results of repeat experiments, including the effect of pretreatment of cells with maleylated P34$_{BSA}$. Rat-2 fibroblasts pretreated with BSA, a control peptide conjugate or maleylated P34$_{BSA}$ developed a sparse and punctuate pattern of Alexa Fluor phalloidin fluorescence upon exposure to 0.5 µM Cytochalasin D or 1 µM Latrunculin B. In contrast, cells that had been pretreated with P34$_{BSA}$ maintained most of their actin filaments. The same result was observed using HGFs (data not shown). Maleic anhydride treatment of P34$_{BSA}$ reversed its protective effects highlighting again the importance of the positive charges on its lysine residues. Notably, the mechanism of action of latrunculin B is distinct from that of cytochalasin D. These findings, combined with those above for Msp, suggest that the actin stabilizing mechanism of P34$_{BSA}$ is not "antagonist"-specific.

Simultaneous exposure to P34$_{BSA}$ conjugate retained its protection when mixed with Latrunculin B but not with Cytochalsin D (data not shown; experimental details were the same as previous in terms of concentration of P33$_{BSA}$ and P34$_{BSA}$).

EXAMPLE 6

Effect of Pretreatment of Fibroblasts with P34$_{BSA}$ Conjugate on Cytoskeletal Effects of *T. denticola*

Figure 10:
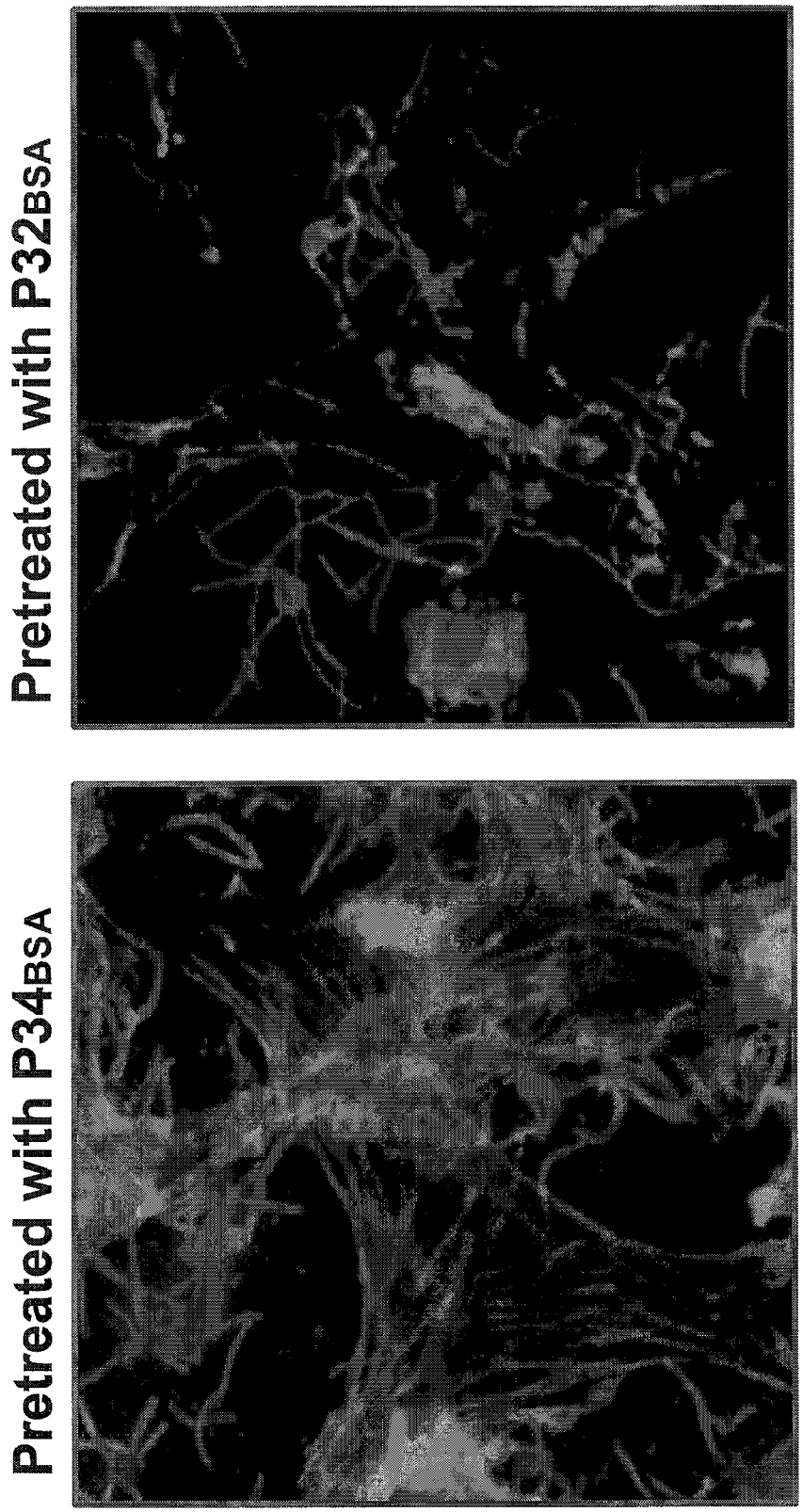
FIG. 10 illustrates the effect of pretreatment with $P34_{BSA}$ on the actions of *T. denticola* on fibroblast cells.

Applicants exposed P34$_{BSA}$ conjugate pretreated fibroblasts to a very dense cell suspension ($10^9$ cells/ml) of *T denticola* whole bacteria, which normally leads to huge cytoskeletal reorganization, cell rounding, and detachment from the substratum. As illustrated in FIG. 10, though not completely protected, there was a surprising degree of maintenance of actin stress fiber and cell structural integrity, even with numerous bacteria attached to the cells.

Rat-2 fibroblasts were grown overnight on chamber slides. The cells were then treated with P34$_{BSA}$ conjugate or P32$_{BSA}$ control conjugate for one hour at 37° C. (50 µg/ml). The cells were washed and incubated with ~$10^9$ cells/ml (OD=0.1) for 1 hour at 37° C. The slide was washed with PBS 3 times and fixed with formaldehyde 3.7%. Actin filaments were stained with Alexa Fluor 488 Phalloidin as described before in FIG. 2. Bacterial cells were stained by using anti-*T. denticola* whole cell (1/500) and Alexa Fluor 594 goat anti rabbit (1/200; as secondary antibody).

EXAMPLE 7

Effect of P34$_{BSA}$ on Expression of RhoA

The mammalian protein Rho is a small GTPase that regulates actin filament assembly, reorganization of pre-existing actin filaments into stress fibers, and the formation of focal adhesions (Chrzanowska-Wodnicka and Burridge, 1996), which affects the number and size of polymerized actin filaments. Using fluorescence imaging methods to detect fluorescence intensity and distribution of expressed immunoreactive RhoA and biochemical western analysis to measure RhoA expression, Applicants found that P34$_{BSA}$ induced significantly increased RhoA expression in fibroblast lysates ($P<0.05$) while RhoA expression was unaffected by control peptide conjugate P33$_{BSA}$ and the BSA control (FIG. 16). This finding is compatible with Applicants' discovery that the specific peptide conjugate P34$_{BSA}$ stabilizes actin, and it provides some information about mechanisms in that P34$_{BSA}$ evidently induces expression of a cellular protein known to promote actin filament polymerization and formation of stress fibers.

Rho activity assay: The amount of active Rho was determined using an affinity precipitation assay as described by Di Ciano-Oliveira et al, 2003. Confluent rat-2 fibroblasts grown in 60-mm dishes were treated as indicated in the respective FIGS. 16A and B legends (50 µg/ml BSA as negative control, 5 µM LPA (lysophosphatidic acid) as positive control, and 50 µg/ml peptide conjugate). Cells were lysed in 800 µl of ice-cold lysis buffer containing 100 mM NaCl, 50 mM Tris base (pH 7.6), 20 mM NaF, 10 mM $MgCl_2$, 1% Triton X-100, 0.5% deoxycholic acid, 0.1% SDS, 20 µl/ml protease inhibitor cocktail (Sigma), 1 mM $Na_3VO_4$, and 1 mM PMSF. The lysates were clarified by centrifugation at 12,000 rpm (1 min, 4° C.). After removing 20 µl sample from each supernatant for determining total Rho, the rest of the supernatants was incubated at 4° C. for 45 min with 10-15 µg of Glutathione-Sepharose beads covered with GST-RBD (Glutathione S-transferase-Rho binding domain), followed by extensive washing. Samples for total Rho and the pelleted beads were diluted in Laemmli sample buffer and boiled for 5 min. The proteins were separated by SDS-PAGE (10% gel), and transferred to nitrocellulose. The blots were blocked with 5% skimmed milk for 2 hours, followed by incubation with anti-Rho A antibody (1:500; Santa Cruz Biotechnology, Santa Cruz, Calif.) for one hour. Binding of the antibody was visualized by peroxidase-coupled anti-mouse antibody (1:3000) and enhanced chemiluminescence.

EXAMPLE 8

Effect of Pretreatment with $P34_{BSA}$ Conjugate on Msp-mediated Diminished Expression of Vinculin in Focal Complexes in Fibroblast Cells Previous experimental results in Applicants' lab have revealed that the average pixel intensity of vinculin staining in Msp-treated cells (in fibroblast on the edge of the incised monolayer of fibroblasts—FIG. 4) is significantly lower than that of control cells up to 2-4 hours after exposure to Msp. With this information, an experiment was designed to examine the effect of the $P34_{BSA}$ peptide conjugate on the distributional change of vinculin upon exposure to Msp. Rat-2 fibroblasts were grown on collagen coated chamber slide overnight. The cells were washed and treated with either $P33_{BSA}$ or $P34_{BSA}$ (50 µg/ml) for one hour at 37° C. Then the cells were washed and treated with Msp (20 µg/ml) for one hour at 37° C. The cells were washed and stained for vinculin as described in FIG. 4.

Figure 11:
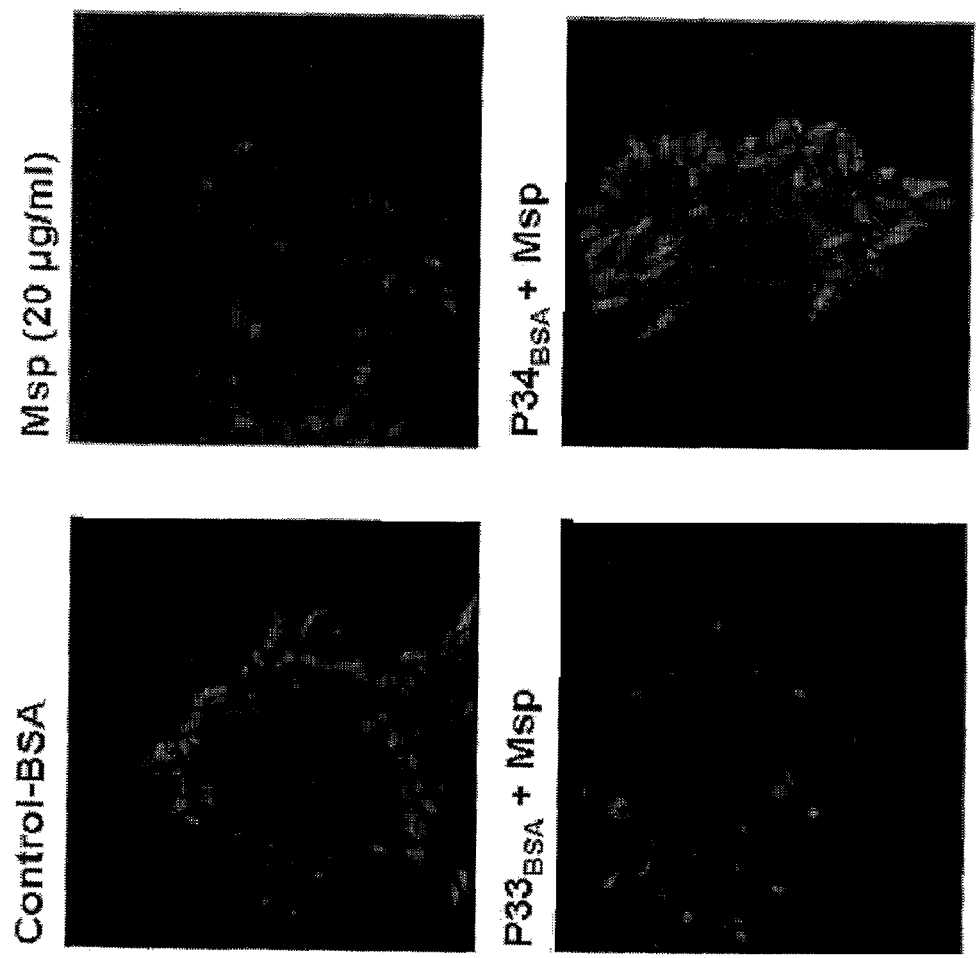
FIG. 11 shows the effect of pretreatment with $P33_{BSA}$ and $P34_{BSA}$ conjugates on Msp-mediated diminished expression of vinculin in focal complexes in fibroblast cells. The distribution of vinculin was maintained when fibroblasts were pretreated with $P34_{BSA}$ conjugate in comparison with control $P33_{BSA}$ treated cells. The $P34_{BSA}$-pretreated cells retained bright fluorescence in discrete focal complex footprints.

Results shown in FIG. 11 illustrate clearly that the distribution of vinculin seen in control cells that were not exposed to Msp was actually maintained when fibroblasts were pretreated with $P34_{BSA}$ conjugate before exposure to Msp. In the other Msp-treated fibroblasts, including the $P33_{BSA}$ conjugate (control peptide)- treated cells, the clarity and intensity of vinculin staining was lower than in control cells that were not exposed to Msp or in the $P34_{BSA}$-pretreated cells. Also, vinculin was observed in a scattered pattern in Msp and $P33_{BSA}$ pretreated cells; Msp treatment of BSA- and $P33_{BSA}$-pretreated cells led to poorly defined foci of vinculin fluorescence. In comparison, nontreated cells and $P34_{BSA}$ pretreated cells retained clearly defined, brightly fluorescent focal adhesions, where there was bright fluorescence in discrete focal complex "footprints" when stained using an immunofluorescence imaging technique.

EXAMPLE 9

Effect of $P34_{BSA}$ Treatment on Migration of Fibroblasts

Mammalian cells migrate on extracellular matrix substrata by the assembly of new focal adhesion complexes and associated actin filaments at the cell's leading edge, while disassembling and reorganizing actin and actin-binding proteins behind the leading edge.

Figure 12A:
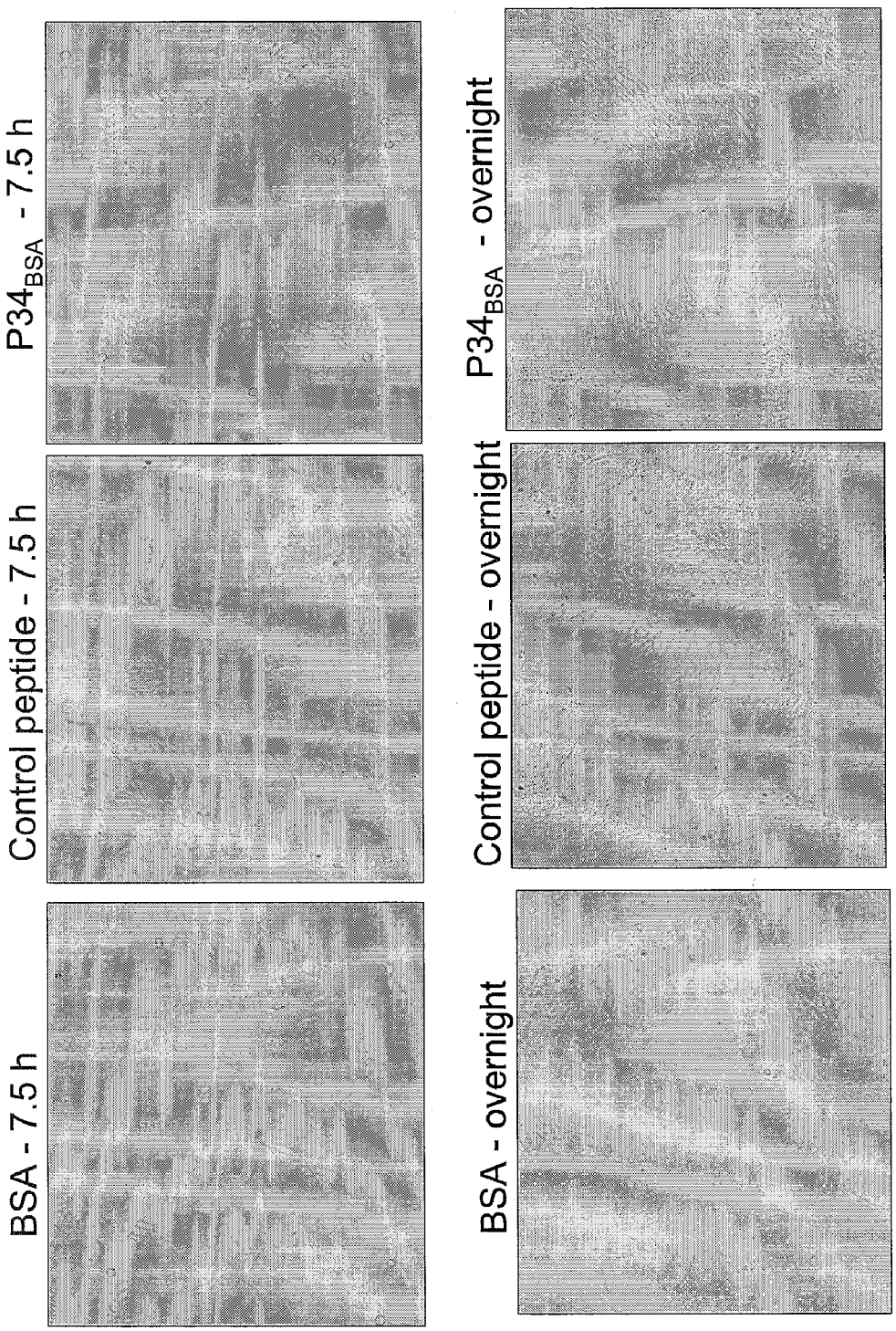
FIGS. 12a and 12b illustrate the effect of $P34_{BSA}$ on migration of fibroblast cells in a wound closure model.
Figure 12B:
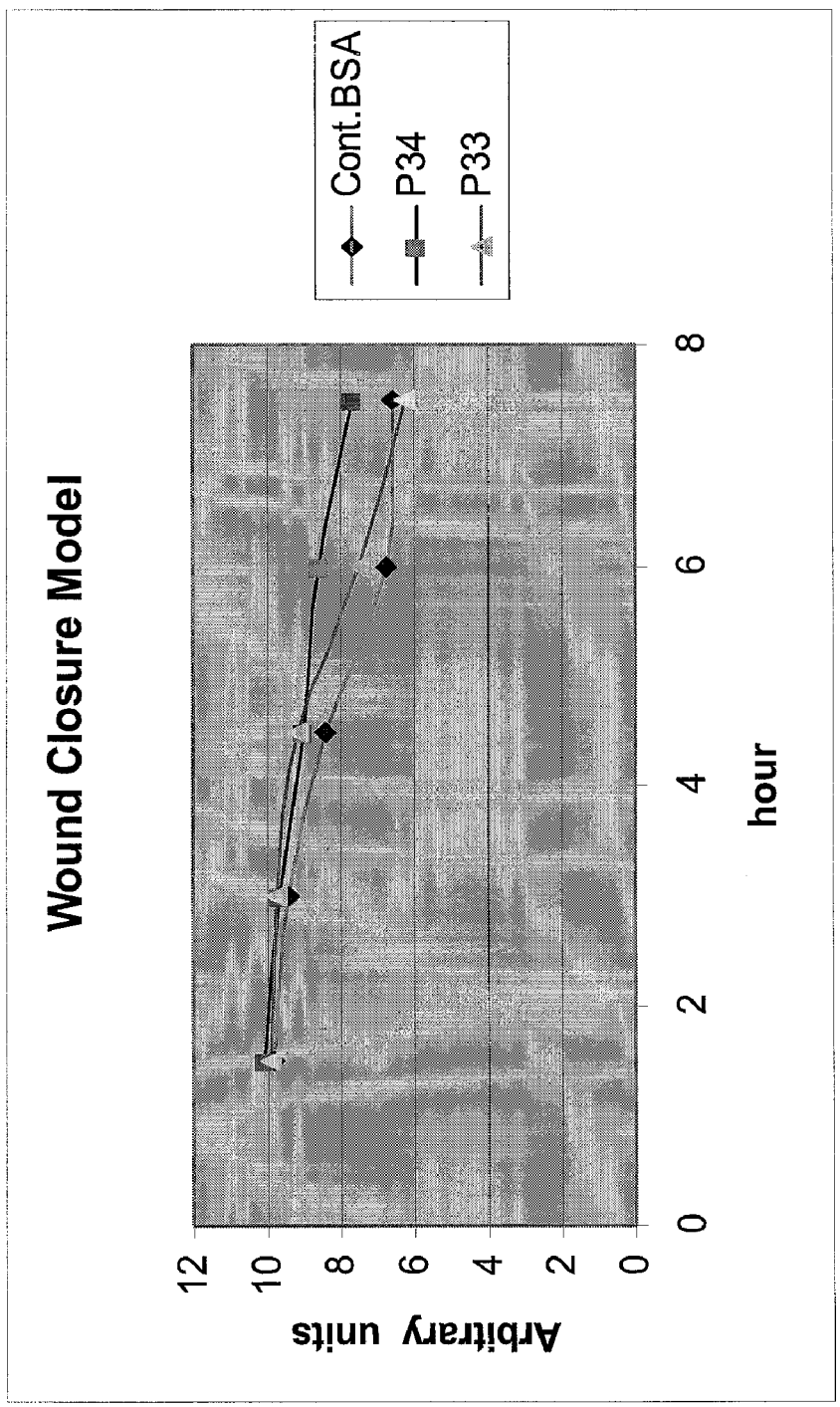

Formation of thicker actin stress fibers, stability of focal adhesion integrity, and activation of Rho by $P34_{BSA}$ were strong indicators that exposure to $P34_{BSA}$ may impact the locomotion of fibroblasts. Thus, a fibroblast migration assay was performed. Applicants tested the effect of the peptide conjugates on fibroblast migration to close an incision in a confluent fibroblast monolayer grown on a collagen matrix, shown in FIGS. 12a and 12b. A confluent monolayer of Rat-2 fibroblasts on type 1 collagen (Vitrogen®, Palo Alto, Calif.)-coated 60-mm dishes was treated with either peptide conjugates or BSA (50 µg/ml in α-MEM) at 37° C. for 1 h and then washed with α-MEM. A uniform scratch wound in the monolayer was made using a cell scraper (Amin et al., 2004). The migration of the cells to close the gap was checked and an image was recorded every 1.5 h over a period of 7.5 h and again after 16 h of growth. The distance between the cells was measured by Image Pro Plus software, and the rate of wound gap closure was calculated (FIG. 12b).

Transient exposure to $P34_{BSA}$, just prior to making a scratch wound in a cell monolayer grown on a collagen substratum, delayed cell migration in comparison with the controls, $P33_{BSA}$ and BSA. The rate of gap closure, analyzed by using the slope of a linear regression curve for $P34_{BSA}$-treated cells (−0.38) was significantly shallower than that for the controls $P33_{BSA}$-treated cells (−0.64) and BSA-treated cells (−0.61). Some cells were able to resume mobility after exposure to $P34_{BSA}$, but they did not close the gap in the monolayer completely during the 16 h experiment.

As illustrated by Example 8, Msp inhibited the recruitment of the actin-binding protein vinculin to focal complexes at the leading edge of fibroblasts, and pretreatment of fibroblasts with peptide conjugate $P34_{BSA}$ protected the cells from reduction of focal complex vinculin when subsequently exposed to Msp. These findings, combined with the present Example, suggest that peptide conjugate $P34_{BSA}$ delays cell migration on extracellular matrices by stabilizing actin filaments and focal complexes at the cell's edge.

EXAMPLE 10

Effect of $P34_{BSA}$ on Polymerization of Actin and Binding of Actin

The ability of $P34_{BSA}$ to induce thicker stress fibers and to localize among actin filaments in fibroblasts suggested that $P34_{BSA}$ may be able to bind actin, nucleate or otherwise stimulate actin polymerization. We used an immunoprecipitation assay to determine whether $P34_{BSA}$ bound actin filaments extracted from Rat-2 cell lysates. An established cell-free system was used to determine whether $P34_{BSA}$ had the capacity to polymerize actin directly (Tang and Janmey, 1996).

In vitro polymerization of G-actin was performed according to the method of Maul and coworkers (Maul et al., 2003).

This in vitro assay is based on the enhanced fluorescence of pyrene-conjugated actin that occurs during polymerization in vitro.

For conducting the polymerization assay, general actin buffer containing pyrene actin and ATP was added to the wells. Then polymerization buffer, samples (P34 free peptide, P33 free peptide, $P34_{BSA}$ and $P33_{BSA}$), and phalloidin (as positive control) were added to the wells. Then fluorescence intensity was read with a spectrophotometer (Excitation: 360 nm; Emission: 410 nm). The reading was done for 15 minutes with intervals of 30 seconds.

For the assay to determine inhibition of polymerization, all the wells contained polymerization buffer to initiate polymerization. Samples (P34 free peptide, P33 free peptide, $P34_{BSA}$ and $P33_{BSA}$) were then added to see whether they could inhibit polymerization of actin monomers.

Details of In vitro Assays

As mentioned above, in vitro polymerization of G-actin was performed according to the method of Maul and coworkers (Maul et al., 2003). 4 µM purified G-actin (pyrene-labeled; Cytoskeleton, Inc., Colorado) in buffer G (0.2 mM $CaCl_2$, 0.2 mM ATP, and 5 mM Tris, pH 8.0) was left at room temperature for 1 h. 25 µl of actin polymerization buffer (50 mM KCl, 2 mM $MgCl_2$, 1 mM ATP, 10 mM Tris, pH 7.5) containing 50 µg/ml of the individual peptide conjugates $P34_{BSA}$ and $P33_{BSA}$ or 50 µg/ml BSA was added to 225 µl pyrene-actin solution and incubated at ambient temperature for 20 min. 0.165 µM Alexa Fluor 488 phalloidin (Molecular Probes, Inc.) was added to the mixture and left in the dark at room temperature for 20 min. 5 µl samples were applied on a microscope slide, and examined by fluorescence microscopy.

$P34_{BSA}$ was tested for the capacity to inhibit or induce actin polymerization. To test for inhibition of actin polymerization, 50 µg/ml $P34_{BSA}$ in polymerization buffer was added to buffer G containing pyrene actin. The fluorescence intensity of the mixture was read with a microplate fluorescence reader (FL600, Bio-Tek®; Ex. 360 nm, +/−20 nm bandwidth; Em. 410 nm, +/−10 nm bandwidth). The emissions were recorded for 15 min at 30 sec intervals. To test $P34_{BSA}$ for induction of polymerization, 50 µg/ml peptide conjugate or 4 µM phalloidin was added to the buffer G containing 1 mM $MgCl_2$ and pyrene actin and monitored for 15 min with the plate reader as explained above.

The ability of $P34_{BSA}$ to bind and to aggregate actin filaments in vitro was also studied using rhodamine actin filaments that had been polymerized in a cell-free system and actin filaments freshly immunoprecipitated from fibroblast cell lysates. Rhodamine non-muscle actin (Cytoskeleton Inc.) was resuspended to 0.5 mg/ml with buffer G supplemented with 0.2 mM ATP. Polymerization buffer containing 50 µg/ml BSA, maleylated $P34_{BSA}$, $P33_{BSA}$ or $P34_{BSA}$ was added as 1/10 of the total volume of rhodamine actin solution, and the mixture was incubated at room temperature for 1 h. The polymerized actin filaments were diluted 100 fold in 1× polymerization buffer containing 70 nM phalloidin, and 1 µl was mixed in a drop of anti-fade solution on a microscope slide.

To prepare cell lysates for actin co-immunoprecipitation, rat-2 fibroblasts were grown overnight in 100-mm cell culture dishes and washed with PBS. 800 µl of cold lysis buffer (50 mM Tris, pH 7.6, 150 mM NaCl, 1% Triton X-100, 1 mM EDTA, 0.2 mM $Na_3VO_4$, and 20 µl/ml protease inhibitor cocktail) was added and the cells were scraped off the dishes and collected in a centrifuge tube. The lysates were centrifuged at 16,000×g for 1 min and equal amounts of supernatants, adjusted by protein concentration, were incubated with 50 µg/ml BSA, maleylated $P34_{BSA}$, or $P34_{BSA}$ for 30 min in a cold-room. 1 µM phalloidin was added to the mixtures and the incubation was continued for another 30 min. 5 µl of anti-P34 antiserum was added to the lysates, and they were incubated in the cold overnight on a rotator. 100 µl of a 33% slurry of protein G Plus/Protein A agarose beads (Calbiochem, San Diego, Calif.) was added and left for 2 h. The suspensions were centrifuged at 16,000×g for 3 min. The supernatant was discarded, and the beads were washed four times with cold PBS, pH 7.4. Immunoprecipitated proteins were diluted with Laemmli sample buffer, boiled for 5 min, and subjected to SDS-PAGE. The separated proteins were transferred to nitrocellulose overnight. Blots were blocked in Tris buffer containing 5% skimmed milk for 2 h and then incubated with mouse monoclonal anti-α-actin antibody (Sigma-Aldrich) for 1 h. Binding of the primary antibody was detected by a 1:3000 dilution of peroxidase-coupled goat anti-mouse antibody (Cedarlane Laboratories Ltd, Hornby, ON) followed by an enhanced chemiluminescence detection method (ECL Plus Western Blotting Detection Reagent, Amersham Biosciences UK Limited).

$P34_{BSA}$ co-precipitated with actin filaments from the fibroblasts, whereas maleic anhydryde-treated $P34_{BSA}$ did not (FIG. 17).

Figure 13A:
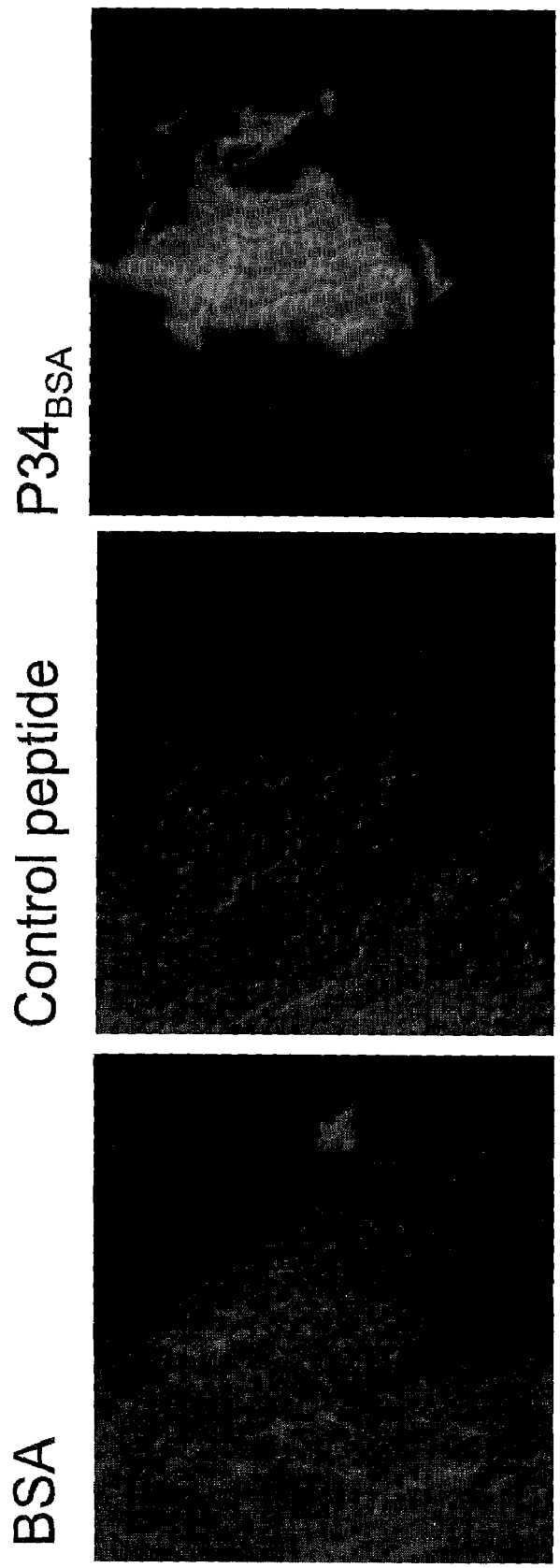
FIGS. 13A and 13B show the effect of $P34_{BSA}$ on actin filaments in vitro. Pre-polymerized rhodamine actin filaments undergo bundle formation in the presence of 50 μg/ml $P34_{BSA}$. In contrast, maleylated $P34_{BSA}$, BSA and $P33_{BSA}$ had no noticeable capacity to aggregate actin filaments.
Figure 13B:
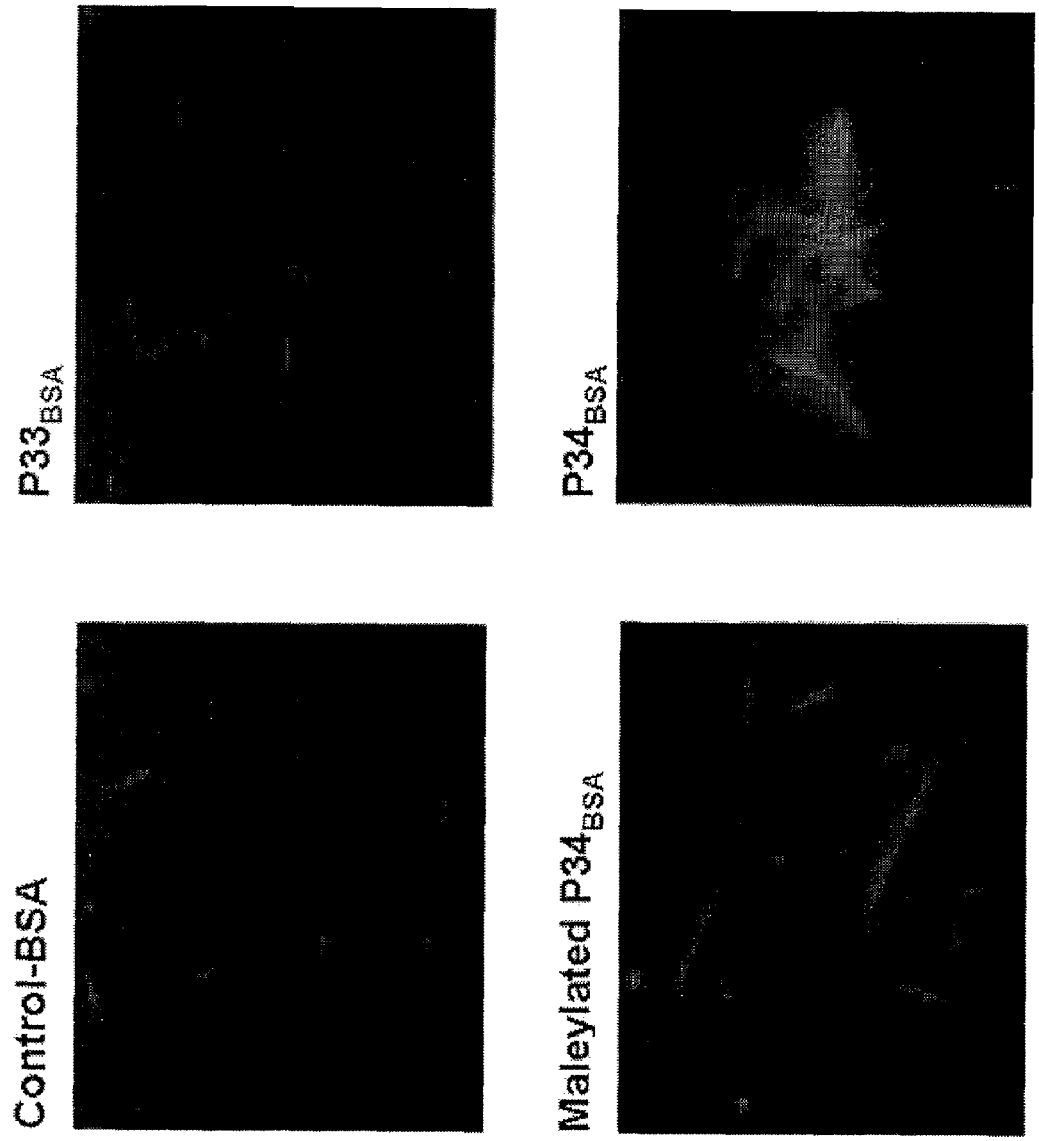

$P34_{BSA}$ neither prevented polymerization of actin in complete polymerization buffer nor caused polymerization in a buffer that supported polymerization by $Mg^{2+}$ (FIGS. 18A and 18B). However, once polymerized, actin filaments were bundled into larger aggregates by $P34_{BSA}$. FIGS. 13A and 13B illustrate the binding and bundling effects of $P34_{BSA}$ on actin filaments (separate experiments). Neither the control peptide conjugate $P33_{BSA}$ nor maleylated $P34_{BSA}$ could aggregate the actin filaments (FIG. 13B). These findings suggest that the capacity of multivalent $P34_{BSA}$ to bind and bridge actin filaments may be a mechanism by which it stabilizes stress fibers in fibroblasts. However, they do not exclude the possibility that $P34_{BSA}$ may also induce actin filament polymerization by activating signal transduction networks of the fibroblasts.

EXAMPLE 11

Testing Anti-peptides and Anti-Msp Against $P34_{BSA}$-conjugate and Msp

Antibodies were raised in rabbits against $P34_{BSA}$ conjugate, $P33_{BSA}$ conjugate, and Msp (which was eluted from the high molecular band on SDS-PAGE). Both anti-peptides could detect the Msp monomers (53 kD band) on Western blots. Also, anti-peptides could detect Msp in ELISA.

When *T. denticola* cells were heat fixed on a glass slide, both anti-P34 and anti-P33 could react with Msp on the surface of the cells. Yet the anti-peptides did not react with antigens on the surface of *T. denticola* cells that were not heat fixed.

Figure 14:
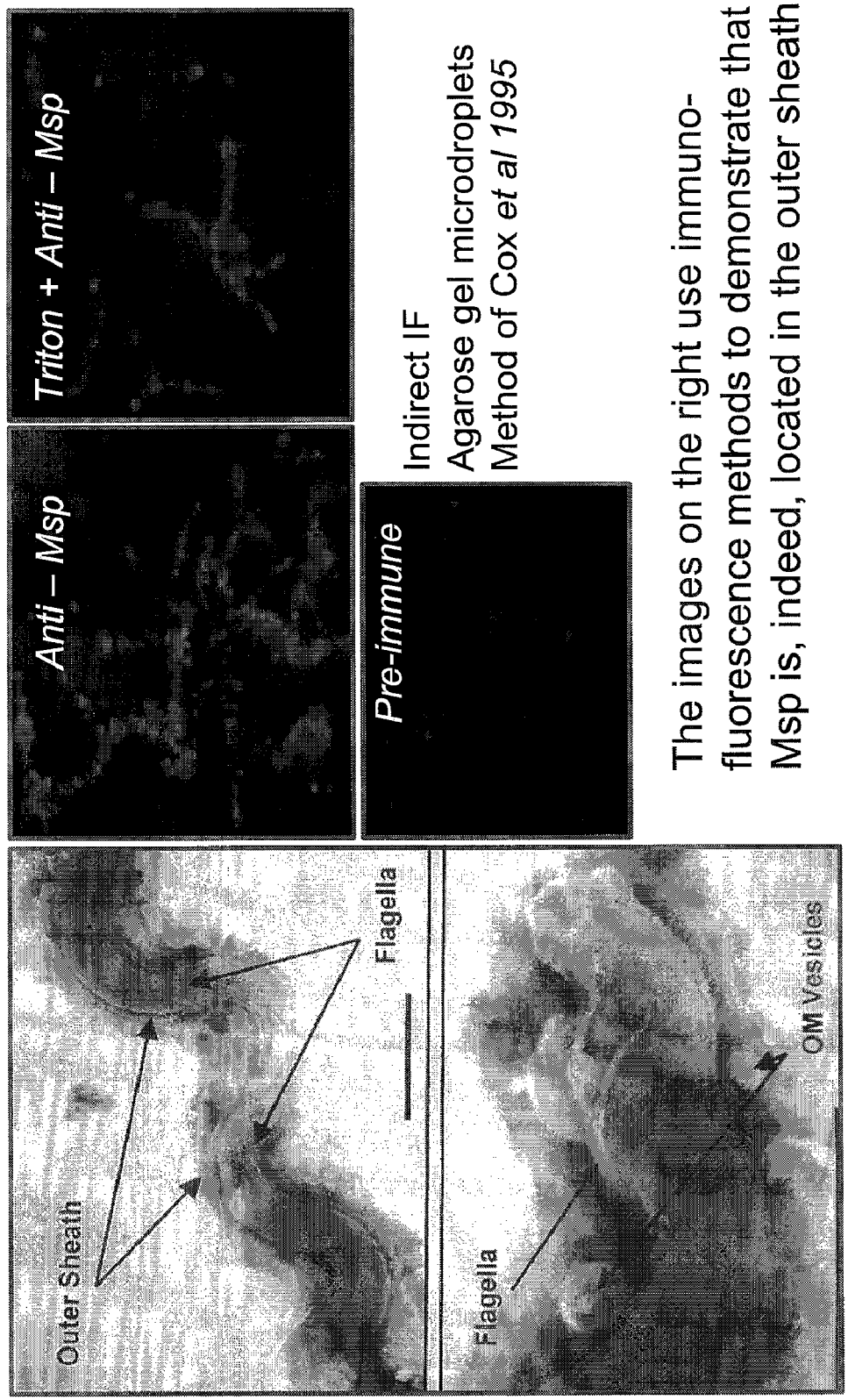
FIG. 14 illustrates the location of Msp in *T. denticola*.

To confirm whether the peptide epitopes or Msp epitopes are exposed on the surface of the outer sheath in intact *T. denticola* cells, Applicants used a well-established gel-encapsulation method that had been developed by David Cox of CDC, Atlanta (1995) for his studies of *Treponema pallidum* antigens (Cox et al., 1995). Anti-peptides could not detect Msp on the surface of the intact *T. denticola* cells (data are not shown) which were encapsulated in gel microdroplets, while anti-Msp detected Msp on the surface of both detergent-permeabilized and nonpermeabilized whole bacteria, more on the non-detergent-treated cells (see FIG. 14)

This result actually provides very good insight bearing on the controversy over the exact cellular location of Msp, since there have been arguments between other laboratories about whether Msp is a surface-exposed protein or if it is an outer membrane protein facing the periplasmic region of the bacterium. The current results help confirm the contention that Msp is surface-exposed.

Yet, by the same method, the current results indicate that the epitopes contained in the P34 and P33 peptides that a bioinformatics approach had predicted may be surface exposed are nonreactive on the intact bacterium. Similarly, they were undetectable in the high molecular mass Msp complex that is prominent as the large size band in PAGE and Western analysis. Thus, P34 and P33 are feasibly exposed domains on Msp monomers, as predicted by the MacVector® analysis, but internally facing when the monomers associate to form the high molecular weight Msp complex on the bacterial surface.

EXAMPLE 12

Locating the Position of the Peptide Conjugate Upon Exposure to Fibroblasts

Observation of thickened actin filaments induced by $P34_{BSA}$ in previous Examples raised a question about its site of action. Thus, the localization of P34$_{BSA}$ was probed. The fibroblasts were grown on an 8-well chamber slide overnight. They were exposed to either P34$_{BSA}$, P33$_{BSA}$, or BSA (50 µg/ml) for 1 h at 37° C. and washed gently to remove unbound peptides. After treatment, the cells were washed gently to remove unbound peptides from the cells. Then the cells were fixed and were either permeabilized (0.1% Triton X-100) or were left intact without permeabilization. For /indirect immunofluorescence, anti-peptide antisera were used as primary antibodies (1/100 in PBS 0.01 M) and goat anti-rabbit Alexa fluor 594-conjugated secondary antibody (1/200 in PBS) was used to detect the immunoreactive peptides. The cells were washed two times with PBS containing 0.01% Tween 20 and once with PBS after each step. All the steps were done at room temperature. The last step was done in a dark room. Permeabilized cells were double labeled with Alexa Fluor 488 phalloidin.

To determine whether a punctate pattern of P34$_{BSA}$ distribution in the permeabilized fibroblasts was due to classical endocytosis, double labeling of the endocytic vesicles and P34$_{BSA}$ was performed (Potocky et al., 2003). Rat-2 cells were washed and incubated for 15 min at 37° C. with 0.5 ml of α-MEM containing 10 µM Alexa Fluor 594 transferrin (Molecular Probes) and either 50 µg/ml BSA, P34$_{BSA}$ or maleylated P34$_{BSA}$. The cells were washed gently with PBS, pH 7.4, placed on ice, and fixed with 3.7% formaldehyde at 4° C. for 1 h. After fixation, the cells were washed, permeabilized and probed for immunoreactive P34$_{BSA}$.

Figure 15A:
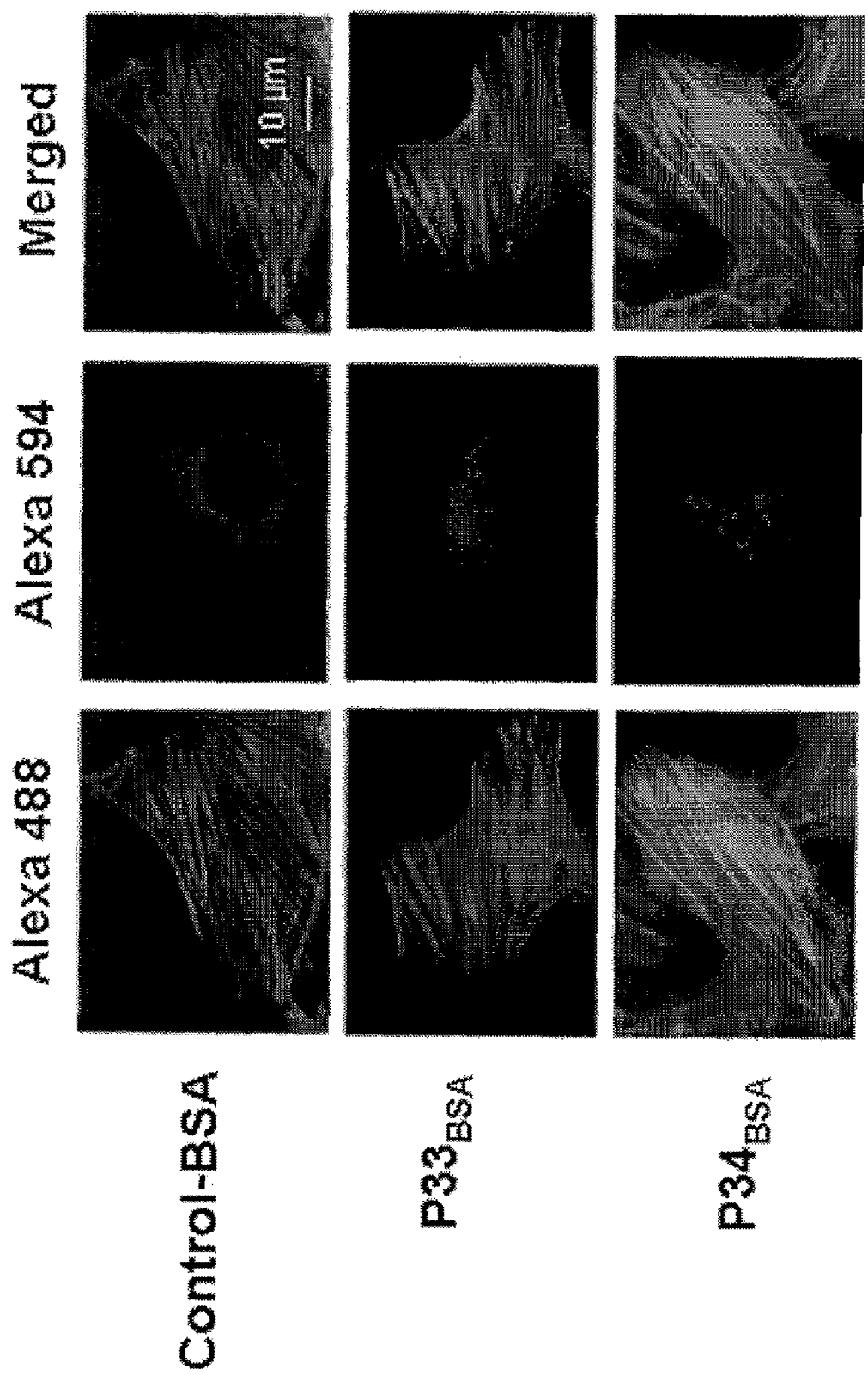
FIGS. 15A-C illustrate the location of $P34_{BSA}$ in fibroblast cells that were exposed to $P34_{BSA}$. After exposure to the peptide conjugates or to BSA, the cells were washed permeabilized with Triton X-100, and analyzed for the location of peptide conjugates by using primary anti-P33 or anti-P34 rabbit antisera followed by goat anti-rabbit Alexa 594-conjugated secondary antibody. The cells were double labeled with Alexa 488 phalloidin to detect actin filaments. Immunolabeled $P34_{BSA}$ was detected only after permeabilization, and it was found co-localized with actin filaments in the merged images (yellow, bottom right panel).
Figure 15B:
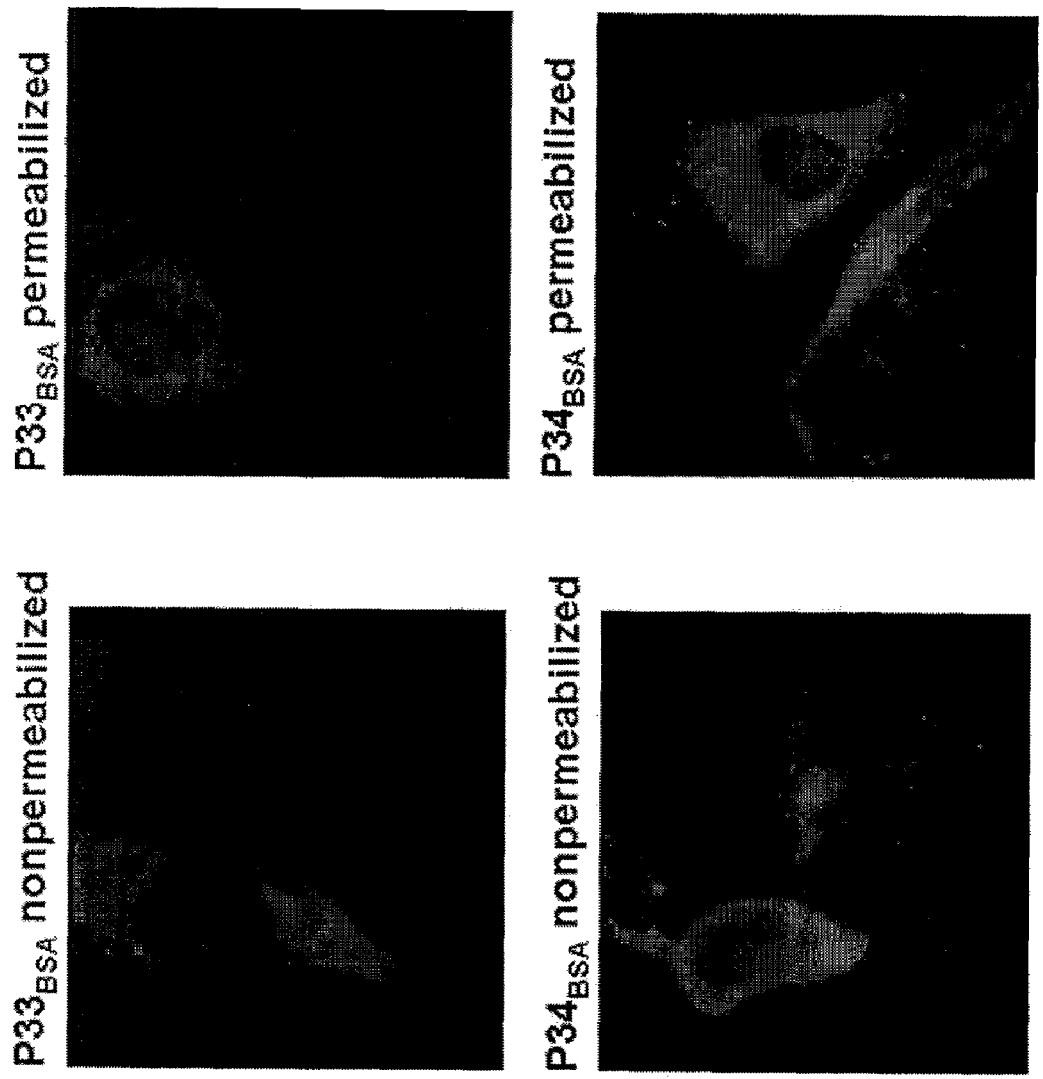

Indirect immunofluorescence microscopy, using a primary antiserum that had been raised against KLH-P34, detected most of the P34$_{BSA}$ conjugate only upon cell permeabilization, i.e. inside the cells (FIGS. 15A and 15B). In contrast, the same method using anti-KLH-P33 antiserum, which had been clearly immunoreactive with P33$_{BSA}$ by ELISA, could not detect P33$_{BSA}$ associated with the cells, neither inside nor on the surface of the cells. These observations suggest that P34$_{BSA}$ is taken up by fibroblasts. The detection of punctate immunoreactive P34$_{BSA}$ among Alexa Fluor 488 phalloidin-labeled stress fibers in these images suggests that P34$_{BSA}$ may actually bind actin filaments in the cytoplasm.

Figure 15C:
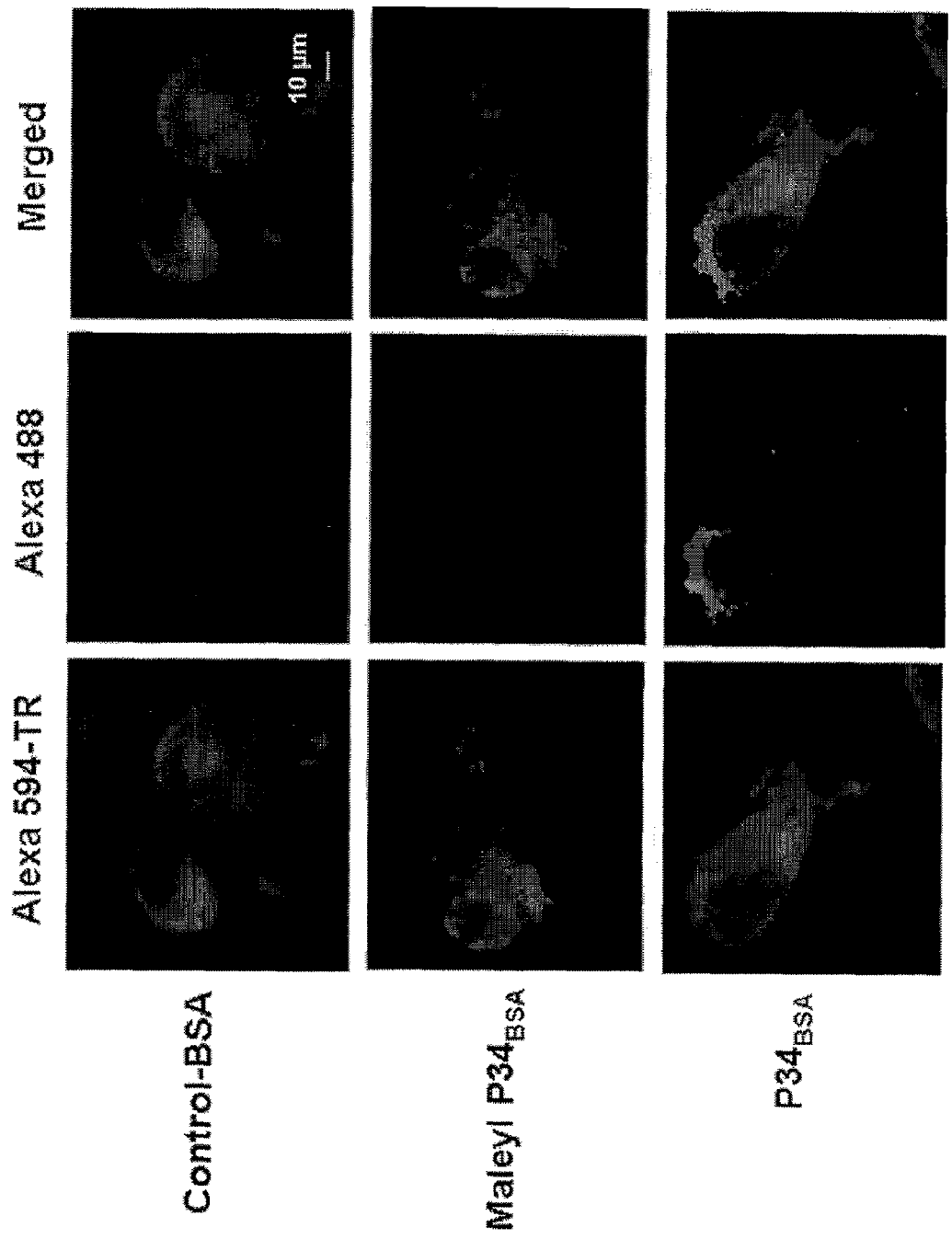

Applicants sought to determine whether P34$_{BSA}$ may be internalized by endocytosis, by dual labeling with Alexa Fluor 594-transferrin (Alexa 594-TR), a well-characterized marker for the endocytic pathway (Qian et al., 2002). The images showed a clear difference and little overlap between the distribution of the Alexa 594-TR and Alexa Fluor 488-labelled P34$_{BSA}$ fluorescent signals (FIG. 15C), indicating that P34$_{BSA}$ was not located in transferrin-containing vesicles and suggesting that its uptake did not require the classic endocytosis pathway that takes up transferrin.

EXAMPLE 13

P34$_{BSA}$ Impairs Neutrophil Chemotaxis

An important question is whether the impact of P34$_{BSA}$ on actin-dependent functions is cell type specific. Applicants selected the neutrophil as an alternative because it is the fastest migrating mammalian cell, and it responds immediately to chemoattractants.

Neutrophil Preparation and Chemotaxis Assay

Murine bone marrow neutrophils were isolated by the method of Allport (Allport et al., 2002). Bone marrow cells were added onto discontinuous Percoll (Sigma) gradients of 80%/65%/55%. Mature neutrophils were recovered by centrifugation (1,800×g) at the 82%/65% interface. The neutrophils were transferred to a separate centrifuge tube and washed with PBS. Purified neutrophils were suspended in Hanks' buffer (0.14 M NaCl, 5.4 mM KCl, 1 mM Tris, 1.1 mM CaCl$_2$, 0.4 mM MgSO$_4$, 1 mM Hepes, pH 7.2). The cells were treated with either peptide conjugates or BSA (50 µg/ml) at room temperature for 30 min. Then 10$^6$ cells in 1% gelatin solution were deposited onto the midline of a glass coverslip and were allowed to adhere for 5 min at 37° C. The coverslips were then rinsed and placed on Zigmond chambers (Zigmond, 1988).

The migration of the neutrophils toward 10$^{-6}$ M fMLP was examined by time-lapse videomicroscopy as described previously (Amin et al., 2004). Images were captured at 20-sec intervals with a Nikon Coolpix 995 camera. Cell tracings were made of each field over time, and the mean path length and speed of 20 cells per group were calculated by cell-tracking software (Retrac, version 2.10).

Results

In the Zigmond chamber model, in which cells migrate laterally from a point of origin up a formyl-Met-Leu-Phe (fMLP) gradient, the P34$_{BSA}$-pretreated neutrophils migrated randomly, relatively close to the origin, whereas the control-pretreated cells migrated further, mostly in the direction of higher fMLP concentrations (FIG. 19). The speed of the P34$_{BSA}$-pretreated neutrophils was significantly lower than that for the P33$_{BSA}$- and the BSA-pretreated cells (P34$_{BSA}$-pretreated cells, 2.55±0.29 µm/min; P33$_{BSA}$-pretreated cells, 6.51±0.46; BSA-pretreated cells, 5.91±0.46; P34$_{BSA}$ versus other two groups $P<0.05$).

Living organisms represent a rich and diverse source of potentially useful reagents, especially if mimetic analogs of naturally expressed molecules can be synthesized. Applicants have demonstrated that P34$_{BSA}$, a synthetic 10-mer peptide modeled on a motif in the deduced amino acid sequence of *T. denticola* Msp and conjugated to BSA, is able to enter fibroblasts and cause them to produce thicker and more stable actin stress fibers. These are properties that are opposite to those of the parent protein Msp (Amin et al., 2004). The Examples described herein using actin filaments freshly extracted from fibroblasts and those polymerized in vitro suggest that P34$_{BSA}$ is able to aggregate actin filaments. P34 has three lysines near the middle and distal end of the peptide when it is conjugated to BSA. Therefore, without being bound by theory, it is believed that multivalent P34$_{BSA}$ has the capacity to bind and bridge anionic moieties of actin filaments via electrostatic interactions. The reversal of the effects by maleic anhydride strengthens this idea, since the maleylated P34$_{BSA}$ was neither able to aggregate filaments of rhodamine actin in the cell-free system, able to bind actin filaments in lysates of fibroblasts, nor able to induce thicker stress fibers within the fibroblasts. The results disclosed herein highlight the importance of the positive charges on the lysine residues of P34$_{BSA}$, and suggest that substituting other positively charged residues at these positions of the peptide may result in other active conjugates. Suitable positively charged residues may include arginine and other positively charged residues commonly known to those of skill in the art.

Cationic peptides are synthesized in nature by diverse organisms, and they are often involved in innate immune responses (Finlay and Hancock, 2004). For example, human cathelicidin LL-37 is an innate immunity modulator that acts in monocytes and epithelial cells (Tjabringa et al., 2003). Actin undergoes bundle formation in vitro in the presence of synthetic LL-37; depolymerization of the filaments by the actin-severing protein gelsolin dissociates the filaments and restores the peptide's bactericidal activity (Weiner et al., 2003). P34$_{BSA}$, which is modeled on a bacterial surface protein, evidently has analogous actin bundling properties.

Though P34$_{BSA}$ aggregated actin filaments but did not polymerize actin in a cell-free system, it is believed that it may activate mediators of actin assembly in live cells, such as the small GTPase Rho. Rho is a key regulator of actin filament assembly, which affects the number and size of polymerized actin filaments as well as the integration of actin in focal adhesions (Ridley, 2001). The Examples herein demonstrate that P34$_{BSA}$ stabilized vinculin-labeled focal adhesions, and it activated Rho in fibroblasts. In cells that have well-organized stress fibers, such as cultured fibroblasts, too high a degree of substratum adhesion through stress fiber-associated focal adhesions may inhibit cell migration (Cox et al., 2001). Using a fibroblast migration assay and a neutrophil chemotaxis assay, it has been demonstrated that P34$_{BSA}$ retarded the migration of two mammalian cell types of different progenitor lineage, which implies that P34$_{BSA}$ has broadly applicable actin-stabilizing properties. The consistent stability of actin filaments of fibroblasts that were exposed to either Msp, cytochalasin D, or latrunculin B also provides substantial evidence that P34$_{BSA}$ has the capacity to protect actin filaments generally.

The best known actin-stabilizing agents come from natural sources. Phalloidin is an oligopeptide found in a few lethal types of *Amanita phalloides* mushrooms. Jasplakinolide is a naturally occurring cyclic peptide that is produced by a sponge, *Jaspis johnstoni*. Similar to phalloidin, it induces actin polymerization and stabilizes pre-existing actin filaments in vitro (Holzinger and Meindl, 1997). Jasplakinolide is also able to permeate the plasma membrane of target cells, which broadens its utility. Amphidinolide H (Amp-H) is a cytotoxic macrolide that was isolated from the dinoflagellate *Amphidinium* (Saito et al., 2004). Amp-H shortens the rate-limiting lag-phase of actin polymerization (Usui et al., 2004). All three cytoskeletal stabilizing agents must be extracted and prepared from biological sources. Thus, the discovery of synthetic laboratory reagents with cytoskeleton-stabilizing properties is highly desirable. A great variety of exogenous and indigenous bacteria that colonize eukaryotic cells have evolved the capacity to exploit or perturb various proteins that comprise and/or regulate the host cytoskeleton (Gouin et al., 2005). Such properties are bound to be encrypted in the structure of their surface or secreted proteins. The expansion of bacterial genomic databases will indubitably provide a very rich resource of molecular models upon which to design effective mimetic agents for modulating the assembly and activity of cytoskeletal proteins. P34 is one such peptide that, when synthesized as a multivalent BSA conjugate, has cytoprotective properties against common actin disrupting agents, as well as its parent protein, Msp.

Thus, in summary, Applicants have demonstrated the use of the peptide conjugate P34$_{BSA}$ for stabilizing the actin cytoskeleton of mammalian cells, and for preventing or controlling migration of mammalian cells. Those skilled in the art will appreciate that, in addition to BSA, there are other potential carriers for the P34 peptide molecule that may be utilized to form conjugates with molecules having potential actin cytoskeleton-stabilizing activity, such as liposomes on which the peptides may be displayed. Since *T. denticola* and its Msp have been found to perturb the actin cytoskeleton of a variety of mammalian cells (rat and human fibroblasts, KB and Hep-2 epithelial cells, and neutrophils, including the locomotion of fibroblasts and neutrophils), and since Cytochalisin D and Latrunculin B have a broad spectrum of targeted cell types in which they actively inhibit actin assembly, it is believed that peptide-conjugates such as P34$_{BSA}$ may have broad applications in stabilizing actin and thus affecting the motility and other functions that depend on actin turn-over of many types of mammalian cells.

All references cited herein are hereby incorporated by reference in their entirety.

The present invention has been described with reference to specific embodiments. Various modifications of the invention in addition to those shown and described herein apparent to those skilled in the art from the preceding description are considered to fall within the scope of the appended claims.

REFERENCES

Aktories, K. and Barbieri, J. T. (2005) Bacterial cytotoxins: targeting eukaryotic switches. *Nat Rev Microbiol.* 3: 397-410.

Allport, J. R., Lim, Y. C., Shipley, J. M., Senior, R. M., Shapiro, S. D., Matsuyoshi, N., et al (2002) Neutrophils from MMP-9- or neutrophil elastase-deficient mice show no defect in transendothelial migration under flow in vitro. *J Leukoc Biol.* 71: 821-828.

Amin M, Ho A C, Lin J Y, Batista da silva A P, Glogauer M, Ellen R P (2004). Induction of de novo subcortical actin filament assembly by *Treponema denticola* major outer sheath protein. Infect Immun 72:3650-4.

Batista da Silva A P, Lee W, Bajenova E, McCulloch C A, Ellen R P (2004). The major outer sheath protein of *Treponema denticola* inhibits the binding step of collagen phagocytosis in fibroblasts. Cell Microbiol 6:485-98.

Bubb M R, Senderowicz A M, Sausville E A, Duncan K L, Korn E D (1994). Jasplakinolide, a cytotoxic natural product, induces actin polymerization and competitively inhibits the binding of phalloidin to F-actin. J Biol Chem 269: 14869-71.

Bubb M R, Spector I, Beyer B B, Fosen K M (2000). Effects of Jasplakinolide on the Kinetics of Actin Polymerization. J Biol Chem 275:5163-70.

Caron, E., Crepin, V. F., Simpson, N., Knutton, S., Garmendia, J. and Frankel, G. (2006) Subversion of actin dynamics by EPEC and EHEC. *Curr Opin Microbiol.* 9: 40-45.

Chrzanowska-Wodnicka, M. and Burridge, K. (1996) Rho-stimulated contractility drives the formation of stress fibers and focal adhesions. *J Cell Biol.* 133: 1403-1415.

Cossart, P. (1997) Host/pathogen interactions. Subversion of the mammalian cell cytoskeleton by invasive bacteria. *J Clin Invest.* 99: 2307-2311.

Cossart, P. and Lecuit, M. (1998) Interactions of *Listeria monocytogenes* with mammalian cells during entry and actin-based movement: bacterial factors, cellular ligands and signaling. *Embo J.* 17: 3797-3806.

Cox D L, Akins D R, Porcella S F, Norgard M V, Radolf J D (1995). *Treponema pallidum* in gel microdroplets: a novel strategy for investigation of treponemal molecular architecture. Mol Microbiol 15:1151-64.

Cox, E. A., Sastry, S. K. and Huttenlocher, A. (2001) Integrin-mediated adhesion regulates cell polarity and membrane protrusion through the Rho family of GTPases. *Mol Biol Cell.* 12: 265-277.

Di Ciano-Oliveira C, Sirokmany G, Szaszi K, Arthur W T, Masszi A, Peterson M, Rotstein O D, Kapus A (2003). Hyperosmotic stress activates Rho: differential involvement in Rho kinase-dependent MLC phosphorylation and NKCC activation. Am J Physiol Cell Physiol 285:C555-66

Ellen R P, Galimanas V B (2005). Spirochetes at the forefront of periodontal infections. Periodontology 2000 38:12-32.

Fabian I, Shur I, Bleiberg I, Rudi A, Kashman Y, Lishner M (1995). Growth modulation and differentiation of acute myeloid leukemia cells by jasplakinolide. Exp. Hematol 23:583-7.

Fenno J C, Muller K H, McBride B C (1996). Sequence analysis, expression, and binding activity of recombinant major outer sheath protein (Msp) of *Treponema denticola*. J Bacteriol 178:2489-97

Fenno, J C, Wong G W, Hannam P M, Müller K H, Leung W K, McBride B C (1997). Conservation of msp, the gene encoding the major outer membrane protein of oral *Treponema* spp. J Bacteriol 179: 1082-89.

Finlay, B. B. and Cossart, P. (1997) Exploitation of mammalian host cell functions by bacterial pathogens. *Science.* 276: 718-725.

Finlay, B. B. and Hancock, R. E. (2004) Can innate immunity be enhanced to treat microbial infections? *Nat Rev Microbiol.* 2: 497-504.

Freshney, R. I. (2005) *Culture of animal cells: a manual of basic technique*. Hoboken, N.J.: Wiley-Liss: 177-193

Gouin, E., Welch, M. D. and Cossart, P. (2005) Actin-based motility of intracellular pathogens. *Curr Opin Microbiol.* 8: 35-45.

Haapasalo M, Muller K-, Uitto B-J, leung W K, and McBride (1992). Characterization, cloning, and binding properties of the major 53-kilodalton *Treponema denticola* surface antigen. Infect Immun 60:2058-65.

Hayward, R. D., Leong, J. M., Koronakis, V. and Campellone, K. G. (2006) Exploiting pathogenic *Escherichia coli* to model transmembrane receptor signalling. *Nat Rev Microbiol.* 4: 358-370.

Holzinger A, Meindl U (1997). Jasplakinolide, a novel actin targeting peptide, inhibits cell growth and induces actin filament polymerization in the green alga *Micrasterias*. Cell Motil Cytoskel 38: 365-372

Lee E, Shelden E A, Knecht D A (1998). Formation of F-actin aggregates in cells treated with actin stabilizing drugs. Cell Motil Cytoskel 39:122-33.

Mathur J, Spielhofer P, Kost B, Chua N (1999). The actin cytoskeleton is required to elaborate and maintain spatial patterning during trichome cell morphogenesis in *Arabidopsis thaliana*. Development 126:5559-68.

Maul, R. S., Song, Y., Amann, K. J., Gerbin, S. C., Pollard, T. D. and Chang, D. D. (2003) EPLIN regulates actin dynamics by cross-linking and stabilizing filaments. *J Cell Biol.* 160: 399-407.

Patel, J. C. and Galan, J. E. (2005) Manipulation of the host actin cytoskeleton by *Salmonella*—all in the name of entry. *Curr Opin Microbiol.* 8: 10-15.

Pender, N. and McCulloch, C. A. (1991) Quantitation of actin polymerization in two human fibroblast sub-types responding to mechanical stretching. *J Cell Sci.* 100 (Pt 1): 187-193.

Potocky, T. B., Menon, A. K. and Gellman, S. H. (2003) Cytoplasmic and nuclear delivery of a TAT-derived peptide and a beta-peptide after endocytic uptake into HeLa cells. *J Biol Chem.* 278: 50188-50194.

Puthengady Thomas, B., Sun, C. X., Bajenova, E., Ellen, R. P. and Glogauer, M. (2006) Modulation of human neutrophil functions in vitro by *Treponema denticola* major outer sheath protein. *Infect Immun.* 74: 1954-1957.

Qian, Z. M., Li, H., Sun, H. and Ho, K. (2002) Targeted drug delivery via the transferrin receptor-mediated endocytosis pathway. *Pharmacol Rev.* 54: 561-587.

Ridley, A. J. (2001) Rho GTPases and cell migration. *J Cell Sci.* 114: 2713-2722.

Rosado J A, Sage S O (2000). A role for the actin cytoskeleton in the initiation and maintenance of store-mediated calcium entry in human platelets. Trends Cardiovasc Med November; 10(8):327-32

Rottner, K., Stradal, T. E. and Wehland, J. (2005) Bacteria-host-cell interactions at the plasma membrane: stories on actin cytoskeleton subversion. *Dev Cell.* 9: 3-17.

Saito, S. Y., Feng, J., Kira, A., Kobayashi, J. and Ohizumi, Y. (2004) Amphidinolide H, a novel type of actin-stabilizing agent isolated from dinoflagellate. *Biochem Biophys Res Commun.* 320: 961-965.

Senderowicz A M, Kaur G, Sainz E, Laing C, Inman W D, Rodriguez J, Crews P, Malspeis L, Grever M R and Sausville E A. Jasplakinolide's inhibition of the growth of prostate carcinoma cells in vitro with disruption of the actin cytoskeleton (1995). JNCI. 87:46-51.

Seshadri R, Myers G S, Tettelin H, Eisen J A, Heidelberg J F, Dodson R J, Davidsen T M, DeBoy R T, Fouts D E, Haft D H, Selengut J, Ren Q, Brinkac L M, Madupu R, Kolonay J, Durkin S A, Daugherty S C, Shetty J, Shvartsbeyn A, Gebregeorgis E, Geer K, Tsegaye G, Malek J, Ayodeji B, Shatsman S, McLeod M P, Smajs D, Howell J K, Pal S, Amin A, Vashisth P, McNeill T Z, Xiang Q, Sodergren E, Baca E, Weinstock G M, Norris S J, Fraser C M, Paulsen I T (2004). Comparison of the genome of the oral pathogen *Treponema denticola* with other spirochete genomes. Proc Natl Acad Sci USA 101:5646-51.

Tang, J. X. and Janmey, P. A. (1996) The polyelectrolyte nature of F-actin and the mechanism of actin bundle formation. *J Biol. Chem.* 271: 8556-8563.

Thomas B P, Sun C X, Bajenova E, Ellen R P, Glogauer M. (2006). Modulation of human neutrophil functions in vitro by *Treponema denticola* major outer sheath protein (Msp). Infect Immun [In press].

Tjabringa, G. S., Aarbiou, J., Ninaber, D. K., Drijfhout, J. W., Sorensen, O. E., Borregaard, N., et al (2003) The antimicrobial peptide LL-37 activates innate immunity at the airway epithelial surface by transactivation of the epidermal growth factor receptor. *J Immunol.* 171: 6690-6696.

Usui, T., Kazami, S., Dohmae, N., Mashimo, Y., Kondo, H., Tsuda, M., et al (2004) Amphidinolide h, a potent cytotoxic macrolide, covalently binds on actin subdomain 4 and stabilizes actin filament. *Chem Biol.* 11: 1269-1277.

Wang Q, Ko K S, Kapus A, McCulloch C, Ellen R P (2001). A spirochete surface protein uncouples store-operated calcium channels in fibroblasts. J Biol Chem 276:23056-64.

Weiner, D. J., Bucki, R. and Janmey, P. A. (2003) The antimicrobial activity of the cathelicidin LL37 is inhibited by F-actin bundles and restored by gelsolin. *Am J Respir Cell Mol. Biol.* 28: 738-745.

Work, T. S. and Burdon, R. H. (1980) *Laboratory techniques in biochemistry and molecular biology*. Amsterdam: Elsevier/North-Holland Biomedical Press.

Zigmond, S. H. (1988) Orientation chamber in chemotaxis. *Methods Enzymol.* 162: 65-72.

We claim:

1. A peptide conjugate consisting of a carrier and one or more identical peptides, wherein each of said one or more identical peptides consists of the peptide sequence YAGKDKNNKA (SEQ ID NO:2) and is conjugated to said carrier through the N-terminus only of said one or more identical peptides.

2. The peptide conjugate as claimed in claim 1, wherein the carrier is bovine serum albumin.

3. The peptide conjugate as claimed in claim 2, wherein said conjugate comprises an average of 6 identical peptides.

4. A method for stabilizing the actin cytoskeleton of mammalian cells comprising the step of exposing said cells to the peptide conjugate as claimed in claim 1.

5. The method as claimed in claim 4, wherein said mammalian cells are fibroblast cells.

6. A method for inhibiting migration of mammalian cells, comprising the step of exposing said mammalian cells to the peptide conjugate as claimed in claim 1.

7. The method as claimed in claim 6, wherein said mammalian cells are fibroblast cells.

8. The method as claimed in claim 6, wherein said mammalian cells are neutrophils.

9. The method as claimed in claim 6, wherein the peptide conjugate is present in a concentration of about 50 μg/ml.

* * * * *